United States Patent
Schachtel

(10) Patent No.: US 12,048,690 B2
(45) Date of Patent: *Jul. 30, 2024

(54) UNIT ORAL DOSE COMPOSITIONS COMPOSED OF NAPROXEN SODIUM AND FAMOTIDINE FOR THE TREATMENT OF ACUTE PAIN AND THE REDUCTION OF THE SEVERITY AND/OR RISK OF HEARTBURN

(71) Applicant: SCHABAR RESEARCH ASSOCIATES LLC, Jupiter, FL (US)

(72) Inventor: Bernard Schachtel, Jupiter, FL (US)

(73) Assignee: SCHABAR RESEARCH ASSOCIATES LLC, Jupiter, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 17/658,849

(22) Filed: Apr. 12, 2022

(65) Prior Publication Data

US 2022/0233509 A1 Jul. 28, 2022

Related U.S. Application Data

(63) Continuation of application No. 17/375,047, filed on Jul. 14, 2021, now Pat. No. 11,324,727.

(60) Provisional application No. 63/052,397, filed on Jul. 15, 2020.

(51) Int. Cl.
| | |
|---|---|
| A61K 31/426 | (2006.01) |
| A61K 9/00 | (2006.01) |
| A61K 31/135 | (2006.01) |
| A61K 31/167 | (2006.01) |
| A61K 31/192 | (2006.01) |

(52) U.S. Cl.
CPC .......... *A61K 31/426* (2013.01); *A61K 9/0053* (2013.01); *A61K 31/135* (2013.01); *A61K 31/167* (2013.01); *A61K 31/192* (2013.01)

(58) Field of Classification Search
CPC .. A61K 31/426; A61K 9/0053; A61K 31/135; A61K 31/167; A61K 31/192
See application file for complete search history.

(56) References Cited

U.S. PATENT DOCUMENTS

| | | | |
|---|---|---|---|
| 4,230,717 A | 10/1980 | Lovelace | |
| 4,279,906 A | 7/1981 | Frosch et al. | |
| 4,283,408 A | 8/1981 | Hirata et al. | |
| 4,554,276 A | 11/1985 | LaMattina | |
| 4,567,183 A | 1/1986 | Sunshine et al. | |
| 4,599,359 A | 7/1986 | Cooper | |
| 4,683,243 A | 7/1987 | Sunshine et al. | |
| 4,755,532 A | 7/1988 | Sunshine et al. | |
| 4,757,060 A | 7/1988 | Lukacsko et al. | |
| 4,783,465 A | 11/1988 | Sunshine et al. | |
| 4,794,112 A | 12/1988 | Cooper | |
| 4,829,064 A | 5/1989 | Sunshine et al. | |
| 4,871,733 A | 10/1989 | Sunshine et al. | |
| 4,975,426 A | 12/1990 | Sunshine et al. | |
| 4,990,535 A | 2/1991 | Cho | |
| 4,994,327 A | 2/1991 | Kato et al. | |
| 5,009,875 A | 4/1991 | Kelley et al. | |
| 5,037,815 A | 8/1991 | Lukacsko et al. | |
| 5,100,675 A | 3/1992 | Cho | |
| 5,102,902 A | 4/1992 | Mercer | |
| 5,204,118 A | 4/1993 | Goldman et al. | |
| 5,229,137 A | 7/1993 | Wolfe | |
| 5,362,737 A | 11/1994 | Vora et al. | |
| 5,417,980 A | 5/1995 | Goldman et al. | |
| 5,541,212 A | 7/1996 | Bourinbaiar | |
| 5,578,597 A | 11/1996 | Spector et al. | |
| 5,594,276 A | 1/1997 | Murari et al. | |
| 5,718,919 A | 2/1998 | Ruddy et al. | |
| 5,763,422 A | 6/1998 | Lichtenberger et al. | |

(Continued)

FOREIGN PATENT DOCUMENTS

| | | |
|---|---|---|
| AU | 2009204360 | 7/2009 |
| EP | 0426479 | 5/1991 |

(Continued)

OTHER PUBLICATIONS

Andersson et al., "Lack of drug-drug interaction between three different non-steroidal anti-inflammatory drugs and omeprazole" Eur. J. Clin. Pharmacol., 1998; 54: 399-404.

Bacracheva et al. Effect of cimetidine on the pharmacokinetics of the metabolites of metamizol. Int. J. Clin. Pharmacol. Ther. 1997; 35(7): 275-281. (abstract only).

Birk et al. "A fixed dose combination of ibuprofen and famotidine," Expert Opinion, 2009, 1385-91. Informa UK Ltd.

Bluhm et al., Potentiation of Opoid Anagesia by H1 and H2 Antagonists, Life Sciences, vol. 31, Issues 12-13, Sep. 1982, pp. 1229-1232.

Busch et al. Interaction of meloxicam with cimetidine, Maalox, or aspirin. J. Clin. Pharmacol. 1996; 36(1): 79-84.

(Continued)

*Primary Examiner* — Robert A Wax
*Assistant Examiner* — Olga V. Tcherkasskaya
(74) *Attorney, Agent, or Firm* — Thomas | Horstemeyer, LLP

(57) ABSTRACT

Described herein are unit oral dose compositions that reduce the severity of heartburn and/or the risk of the occurrence of heartburn in a human in need of taking naproxen sodium for the OTC treatment of acute pain wherein the human is not experiencing heartburn prior to the oral administration of the unit oral dose composition comprising orally administering to the human of a unit oral dose composition comprising (i) naproxen sodium at a dosage from about 100 mg to about 440 mg per unit oral dose composition and (ii) famotidine at a dosage from about 3 mg to about 20 mg per unit oral dose composition, wherein the dissolution rate of famotidine in the unit oral dose composition in said human at a specified time within 45 minutes of administration of said unit oral dose composition to said human is greater than the dissolution rate of naproxen sodium in the unit oral dose composition in said human at the same specified time.

13 Claims, No Drawings

(56) References Cited

U.S. PATENT DOCUMENTS

| | | | |
|---|---|---|---|
| 5,805,580 A | 9/1998 | Vercauteren et al. | |
| 5,955,451 A | 9/1999 | Lichtenberger et al. | |
| 5,993,327 A | 11/1999 | Terril | |
| 6,004,582 A | 12/1999 | Faour et al. | |
| 6,027,746 A | 2/2000 | Lech | |
| 6,130,233 A | 10/2000 | Woosley et al. | |
| 6,146,661 A | 11/2000 | Hoshino | |
| 6,160,020 A | 12/2000 | Ohannesian et al. | |
| 6,187,795 B1 | 2/2001 | Woosley et al. | |
| 6,248,363 B1 | 6/2001 | Patel et al. | |
| 6,261,602 B1 | 7/2001 | Calanchi et al. | |
| 6,270,807 B1 | 8/2001 | Danielson et al. | |
| 6,294,192 B1 | 9/2001 | Patel et al. | |
| 6,303,632 B1 | 10/2001 | Woosley et al. | |
| 6,384,038 B1 | 5/2002 | Rubin | |
| 6,384,054 B1 | 5/2002 | Woosley et al. | |
| 6,395,300 B1 | 5/2002 | Straub et al. | |
| 6,417,184 B1 | 7/2002 | Ockert | |
| 6,471,991 B2 | 10/2002 | Robinson et al. | |
| 6,552,047 B2 | 4/2003 | Garvey et al. | |
| 6,589,551 B1 | 7/2003 | Jolliffe | |
| 6,589,556 B2 | 7/2003 | Cherukuri | |
| 6,596,298 B2 | 7/2003 | Leung et al. | |
| 6,610,667 B1 | 8/2003 | Dettmar et al. | |
| 6,627,235 B2 | 9/2003 | Vandamme et al. | |
| 6,656,482 B2 | 12/2003 | Mehta et al. | |
| 6,663,893 B2 | 12/2003 | Corbo et al. | |
| 6,713,089 B1 | 3/2004 | Bertelsen et al. | |
| 6,773,721 B1 | 8/2004 | Wong et al. | |
| 6,926,907 B2 | 8/2005 | Plachetka | |
| 6,951,871 B2 | 10/2005 | Aslanian et al. | |
| 7,105,505 B2 | 9/2006 | Zeng et al. | |
| 7,186,753 B1 | 3/2007 | Del Soldato | |
| 7,220,735 B2 | 5/2007 | Ting et al. | |
| 7,271,266 B2 | 9/2007 | Finke et al. | |
| 7,300,941 B2 | 11/2007 | Aslanian et al. | |
| 7,323,129 B2 | 1/2008 | Sowden et al. | |
| 7,361,006 B2 | 4/2008 | Sowden et al. | |
| 7,407,669 B2 | 8/2008 | Leung et al. | |
| 7,429,575 B2 | 9/2008 | Yu et al. | |
| 7,482,469 B2 | 1/2009 | Palin et al. | |
| 7,670,612 B2 | 3/2010 | Miller | |
| 7,678,387 B2 | 3/2010 | Cherukuri | |
| 7,678,786 B2 | 3/2010 | Kuo et al. | |
| 7,744,908 B2 | 6/2010 | Asotra et al. | |
| 7,749,533 B2 | 7/2010 | Fu et al. | |
| 7,772,232 B2 | 8/2010 | Johnson et al. | |
| 8,067,033 B2 | 11/2011 | Xu et al. | |
| 8,067,451 B2 | 11/2011 | Tidmarsh et al. | |
| 8,309,127 B2 | 2/2012 | Xu et al. | |
| 8,318,202 B2 | 11/2012 | Xu et al. | |
| 8,449,910 B2 | 5/2013 | Xu et al. | |
| 8,449,912 B2 | 5/2013 | Shriram et al. | |
| 8,501,228 B2 | 8/2013 | Xu et al. | |
| 8,771,643 B2 | 7/2014 | Schachtel | |
| 9,044,465 B2 | 6/2015 | Schachtel | |
| 2003/0069255 A1 | 4/2003 | Plachetka | |
| 2003/0130263 A1 | 7/2003 | Hirsh | |
| 2004/0029864 A1 | 2/2004 | MacMillan | |
| 2005/0008690 A1 | 1/2005 | Miller | |
| 2005/0095197 A1 | 5/2005 | Tuszynski et al. | |
| 2005/0163847 A1 | 7/2005 | Cheng et al. | |
| 2005/0266032 A1 | 12/2005 | Srinivasan et al. | |
| 2006/0034943 A1 | 2/2006 | Tuszynski | |
| 2007/0043096 A1 | 2/2007 | Tidmarsh et al. | |
| 2007/0043097 A1 | 2/2007 | Tidmarsh et al. | |
| 2007/0154542 A1 | 7/2007 | Tananbaum et al. | |
| 2008/0020040 A1 | 1/2008 | Tidmarsh et al. | |
| 2008/0021078 A1 | 1/2008 | Tidmarsh et al. | |
| 2008/0050427 A1 | 2/2008 | Burch et al. | |
| 2008/0063706 A1 | 3/2008 | Tidmarsh et al. | |
| 2008/0085314 A1 | 4/2008 | Shalaby | |
| 2008/0091957 A1 | 4/2008 | Everett et al. | |
| 2009/0142393 A1 | 6/2009 | Xu et al. | |
| 2009/0233970 A1 | 9/2009 | Nickell et al. | |
| 2009/0264484 A1 | 10/2009 | Tidmarsh et al. | |
| 2009/0275622 A1 | 11/2009 | Linga et al. | |
| 2010/0227854 A1 | 9/2010 | Tananbaum et al. | |
| 2010/0297224 A1 | 11/2010 | Tidmarsh et al. | |
| 2011/0313009 A1 | 12/2011 | Tidmarsh et al. | |
| 2016/0128944 A1 | 5/2016 | Chawrai et al. | |
| 2022/0125732 A1 | 4/2022 | Gumudavelli et al. | |

FOREIGN PATENT DOCUMENTS

| | | |
|---|---|---|
| EP | 0663839 | 7/1995 |
| EP | 2043637 | 1/2012 |
| WO | 1992005783 | 3/1992 |
| WO | 1994007541 | 4/1994 |
| WO | 2000035298 | 6/2000 |
| WO | 2001043722 | 6/2001 |
| WO | 2003026627 | 4/2003 |
| WO | 2005063219 | 7/2005 |
| WO | 2006052856 | 5/2006 |
| WO | 2007072503 | 6/2007 |
| WO | 2008011426 | 1/2008 |
| WO | 2008070268 | 6/2008 |

OTHER PUBLICATIONS

Dammann et al. Differential effects of misoprostil and ranitidine on the pharmacokinetics of diclofenac and gastrointestinal symptoms. Br. J. Clin. Pharmacol. 1993; 36(4): 345-349.

Delhotal-Landes et al. Pharmacokinetic interations between NSAIDs (indomethacin or sulindac) and H2-receptor antagonists (cimetidine or ranitidine) in human volunteers. Clin. Pharmacol. Ther. 1988; 44 (4): 442-452.

Dixon et al. A lack of pharmacokinetic interaction between ranitidine and piroxicam. Eur. J. Clin. Pharmacol. 1990; 39(6): 583-586.

Evans et al., "Lack of effect of cimetidine on the pharmacokinetics of R-(−) and S-(+) ibuprofen" Br. J. Clin. Pharmacol., 1989; 28: 143-149.

Forsyth et al., Do Nizatidine and Cimetidine Interact with Ibuprofen? 1988, Eur. J. Clin. Pharmacol., 35: 85-88.

Hough et al. "Novel Qualitative Structure-Activity Relationships for the Antinociceptive Actions of H2 Antagonists, H3 Antagonists and Derivatives," The Journal of Pharmacology and Experimental Therapeutics, 1997, 1534-43.

Kendall et al., "Coadministration of misoprostol or ranitidine with indomethacin: effects on pharmacokinetics, abdominal symptoms and bowel habit" Aliment Pharmacol. Ther. 1992; 6;437-446.

Laska et al. "The correlation between blood levels of ibuprofen and clinical analgesic response," Clinical Pharmacology and Therapeutics, 1986, 1-7. (abstract only).

Leucuta et al. No effect of short term ranitidine on diclofenac pharmacokinetics. Rom. J. Gastroenterol. 2004; 13 (4): 306-308.

Milligan et al. The consequences of H2 receptor antagonist-piroxicam coadministration in patients with joint disorders. Eur. J. Clin. Pharmacol. 1993: 45(6): 507-512.

Ochs et al. "Interaction of ibuprofen with the H-2 receptor antagonists ranitidine and cimetidine," Clinical Pharmacology and Therapeutics, 1985, 648-51.

Parrott et al. "Influence of cimetidine on the disposition of ibuprofen in the rat," Research Communications in Chemical Pathology and Pharmacology, 1984, 369-80. (abstract only).

Raffa "Antihistamines as analgesics," Journal of Clinical Pharmacology and Therapeutics, 2001, 81-5.

Ravic et al. A pharmacokinetic interaction between cimetidine or ranitidine and lornoxicam. Postgrad. Med. J. 1993; 69: 865-866.

Rumore et al., "Clinical Efficacy of Antihistaminics as Analgesics," Pain, 25, 1986, pp. 7-22.

Said et al. Influence of cimetidine on the pharmacokinetics of piroxicam in rat and man. Arzneimittelforschung 1989; 39(7): 790-792. (abstract only).

Santiago-Palma et al. "Diphenhyramine as an Analgesic Adjuvant in Refractory Cancer Pain", Journal of Pain and Symptom Management, 2001, vol. 22., No. 2, pp. 699-703, Elsevier, New York.

(56) References Cited

OTHER PUBLICATIONS

Schachtel et al., 1984, "Rating Scales for Analgesics in Sore Throat," Clin. Pharmacaol. & Therapeut., 36(2): 151-156.
Schachtel et al., 1988, "Sore Throat Pain in the Evaluation of Mild Analgesics," Clin. Pharmacol. & Therapeut., 44(6): 704-711.
Schachtel et al., 1993, "A placebo-controlled model for assaying systemic analgesics in children," Clin. Trials & Therapeut., 593-601.
Schachtel et al., 2002, "Demonstration of dose response of flurbiprofen lozenges with the sore throat pain model," Clin. Pharmacol. & Therapeut. 71:375-380.
Schachtel et al., 2007, "Utility and Sensitivity of the Sore Throat Pain Model: Results of a Randomized Controlled Trial on the COX-2 Selective Inhibitor Valdecoxib," J. Clin. Pharmacol 47:860-870. (Originally published online May 24, 2007).
Schachtel, 1991, "Sore Throat Pain," Advances in Pain Research and Therapy, vol. 18, ed. M. Max, R. Portenoy, & E. Laska, New York: Raven Press, Ltd., pp. 393-407.
Shamburek et al, "Control of gastric acid secretion. Histamine H2-receptor antagonists and H+K(+)-ATPase Inhibitors." Medical College of Virginia, Richmond, Gastroenterol Clinic North America, Sep. 1992, 21(3):527-50. (abstract only).
Singh et al., "Gastrointestinal Tract Complications of Nonsteroidal Anti-inflammatory Drug Treatment in Rheumatoid Arthritis" Arch. Intern. Med., 1996; 156: 1530-1536.
Small et al., "Influence of H2-receptor antagonists on the disposition of flurbiprofen enantiomers" J. Clin. Pharmacol. 1990; 30: 660-664.
Verbeeck et al. "Single and multiple dose pharmacokinetics of enteric coated ketoprofen: effect of cimetidine" Eur. J. Clin. Pharmacol. 1988; 35: 521-527.
Vimovo: (naproxen/esomeprazole magnesium) Delayed-released tablets, Pharmacy & Therapeutics, 2010, 35(9 Section 2): 2-4.
Vovk et al. "The modification of the pharmacokinetics and analgesic effect of naproxen by cimetidine, phenobarbital and thiamine diphosphate," Experiments in Clinical Pharmacology, 1996, 35-7. (abstract only).
Vree et al. The effects of cimetidine, ranitidine, and famotidine on the single-dose pharmacokinetics of naproxen and its metabolites in humans. Int. J. Clin. Pharmacol. Ther. Toxicol. 1993; 31(12): 597-601.
Vree et al. The pharmacokinetics of naproxen, its metabolite O-desmethylnaproxen, and their acyl glucuronides in humans. Effect of cimetidine. Br. J. Clin. Pharmacol. 1993; 35(5): 467-472.
Australian Examination Report for application No. 2009204360 dated Apr. 26, 2013.
First Examination Report dated Feb. 22, 2011 for New Zealand application No. 587202.
Second Examination Report dated Jun. 13, 2012 for New Zealand application No. 587202.
European Search Report dated Dec. 8, 2011 for EP application No. 09700489.9.
International Search Report and Combination Written Opinion in re PCT/US2009/30079, mailed Feb. 26, 2009.
Satterwhite, J.H. et al, "Nizatidine: Lack of Drug Interaction with Naproxen," 1992, Clin. Res., 40:706A.
Australian Examination Report for 2015201278 dated Apr. 8, 2016.
Canadian Office Action for 2,930,063 dated Jun. 8, 2016.
Extended European Search Report for 16169955.8 dated Oct. 10, 2016.
International Search Report and Written Opinion for PCT/US2021/041521 mailed Nov. 18, 2021.
Laine LA et al: "407 Does High-Dose Famotidine Reduce Gastric and Duodenal Ulcers in NSAID Users? Two Double-Blind Six-Month Trials of Single-Tablet Combination Ibuprofen-Famotidine vs. Ibuprofen Alone (Reduce-1 and 2)", Gastroenterology, Elsevier Inc, US, vol. 136, No. 5, May 1, 2009 (May 1, 2009), pp. A-69, XP026110857, ISSN: 0016-5085, DOI: 10.1016/S0016-5085(09)60310-3 [retrieved on May 1, 2009] the whole document.
Sevelius H. et al."Bioavailability of Naproxen Sodium and Its Relationship to Clinical Analgesic Effects" The Institutes of Clinical Medicine and Pharmacology and Metabolism, Syntex Research, Palo Alto, California and Division of Clinical Pharmacology, University of Cincinnati Medical Center, Cincinnati, Ohio, USA. Br. J. clin. Pharmac. (1980), 10, 259-263.
Bernadette DeArmond "Safety Profde of Over-the-Counter Naproxen Sodium" Clinical Tiibrapeutics•Nol. 17, No. 4, 1995 p. 587-601.

UNIT ORAL DOSE COMPOSITIONS COMPOSED OF NAPROXEN SODIUM AND FAMOTIDINE FOR THE TREATMENT OF ACUTE PAIN AND THE REDUCTION OF THE SEVERITY AND/OR RISK OF HEARTBURN

CROSS-REFERENCE TO RELATED APPLICATIONS

This application is a continuation application of U.S. Nonprovisional patent application Ser. No. 17/375,047, filed on Jul. 14, 2021, which claims the benefit of and priority to U.S. Provisional Patent Application No. 63/052,397, filed on Jul. 15, 2020, the contents of which are incorporated by reference herein in their entireties.

BACKGROUND

While generally regarded as safe, effective treatments for acute pain and fever, the use of non-prescription-strength, or over-the-counter (OTC), non-steroidal anti-inflammatory drugs (NSAIDs) like naproxen sodium can be associated with stomach problems such as heartburn. In fact, the package labeling approved by the U.S. Food and Drug Administration for OTC NSAIDs, including naproxen sodium, draws attention to "stomach problems such as heartburn" and advises consumers to "take with food or milk if stomach upset occurs."

SUMMARY

Described herein are unit oral dose compositions that reduce the severity of heartburn or the risk of the occurrence of heartburn in a human in need of taking naproxen sodium for the OTC treatment of acute pain wherein the human is not experiencing heartburn prior to the oral administration of the unit oral dose composition comprising orally administering to the human of a unit oral dose composition comprising (i) naproxen sodium at a dosage from about 100 mg to about 440 mg per unit oral dose composition and (ii) famotidine at a dosage from about 3 mg to about 20 mg per unit oral dose composition, wherein the dissolution rate of famotidine in the unit oral dose composition in said human at a specified time within 45 minutes of administration of said unit oral dose composition to said human is greater than the dissolution rate of naproxen sodium in the unit oral dose composition in said human at the same specified time.

Other advantages of the present disclosure will be or become apparent to one with skill in the art upon examination of the following detailed description. It is intended that all such additional advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

DETAILED DESCRIPTION

Before the present compounds, compositions, articles, devices, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of".

As used in the specification and the appended claims, the singular forms "a," "an" and "the" include plural referents unless the context clearly dictates otherwise. Thus, for example, reference to "an inert excipient" includes, but are not limited to, mixtures or combinations of two or more such inert excipients, and the like.

It should be noted that ratios, concentrations, amounts, rates, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed and "about 5 to about 15" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

It should be noted that ratios, concentrations, amounts, rates, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

As used herein, the terms "optional" or "optionally" means that the subsequently described event or circumstance can or cannot occur, and that the description includes instances where said event or circumstance and instances where it does not.

"Famotidine" is 3-[2-(diaminomethyleneamino)thiazol-4-ylmethylthio]-N-sulfamoylpropionamidine, including polymorphic forms such as those designated Form A and Form B (see, e.g., U.S. Pat. Nos. 5,128,477 and 5,120,850) and their mixtures.

"Naproxen sodium" is the sodium salt of (+)-(S)-2-(6-methoxynaphthalen-2-yl) propanoic acid.

As used herein, "unit oral dose composition" refers to physically discrete units suitable for use in a human, each unit containing a predetermined quantity of famotidine and a predetermined quantity of naproxen sodium calculated to produce the desired response or responses in association with its administration.

The term "immediate-release" or "immediate release" refers to the release of famotidine and/or naproxen sodium quickly after oral administration of the unit dose composition to the human.

As used herein, "treatment regimen" refers to the administration of the unit oral dose composition at the same dosage to a human over a period of time. For example, a human may initially be administered one tablet of the unit oral dose composition for a total of 1 tablet unit oral dose composition over a 24-hour period. In one aspect, a human may initially be administered one tablet of the unit oral dose composition, then administered one tablet of the unit oral dose composition within 1 hour after the initial administration, for a maximum total of 2 tablet unit oral dose compositions over a 24-hour period. In another aspect, a human may initially be administered one tablet of the unit oral dose composition, then administered one tablet of the unit oral dose composition within 1 hour after the initial administration, then administered one tablet of the unit oral dose composition 8 to 12 hours later, for a maximum total of 3 tablet unit oral dose compositions over a 24-hour period.

The term "heartburn" is also known as pyrosis, cardialgia or acid indigestion. Symptoms of heartburn include, but are not limited to, a burning sensation in the central chest or upper central abdomen, which can be a source of pain to the subject. The pain or discomfort often rises in the chest and may radiate to the neck, angle of the arm, or throat, leaving a sour, acidic or salty taste in the back of the throat. Heartburn is usually due to regurgitation of gastric acid (gastric reflux) into the esophagus and is the major symptom of gastroesophageal reflux disease (GERD). Heartburn can be caused by hiatal hernia, pregnancy, being overweight or a smoker, certain medications (e.g., NSAIDs like naproxen sodium, ibuprofen, acetylsalicylic acid), large meals, certain foods (such as onions or citrus fruits), lying down with a full stomach, stress, etc.

The term "treat or treatment" as used herein is defined as reducing the occurrence and/or severity of one or more symptoms when the human is administered a unit oral dose composition as described herein when compared to the same symptom(s) in the absence of the administration of the unit oral dose composition to the human, specifically, preventing the occurrence of naproxen sodium-induced heartburn and/or reducing the severity of naproxen sodium-induced heartburn.

The term "prevent or prevention" as used herein is defined as eliminating or reducing the likelihood, or risk, of the occurrence and/or severity of one or more symptoms when the human is administered a unit oral dose composition as described herein when compared to the same symptom(s) in the absence of the administration of the unit oral dose composition to the human.

The term "acute pain" is pain that is not persistent, generally lasts a brief period of time (e.g., hours, 1-3 days, 1 week), and is resolved quickly. Examples of acute pain include, but are not limited to, acute pain of inflammation (including menstrual cramps, or dysmenorrhea), acute pain or stiffness of rheumatic or arthritic conditions ("flares" of osteoarthritis), minor pain of arthritis, acute joint and body pains, acute muscular aches and strains, acute pain of ligamentous sprains (including sprained ankle), acute backache, minor aches and pains due to the common cold (including acute sore throat of infectious or non-infectious origin and sinus pain), minor aches and pains due to fever (including muscle achiness, or myalgia), acute headache (including tension-type and acute migraine), acute pain of minor surgery (including acute pain of dental extractions), acute toothache, occasional sleeplessness when associated with minor aches and pains, or any combination thereof.

The term "chronic pain" is pain that is persistent, generally lasts more than three months, up to years, and is not resolved quickly. An example of chronic pain includes pain caused by cancer or by metastases of cancer throughout the body, in particular, to bones. Other examples include chronic non-malignant pain, chronic neurologic diseases such as nerve impingement, spinal stenosis and other skeletal diseases of the back and limbs, chronic arthritis such as osteoarthritis, rheumatoid arthritis and psoriatic arthritis, chronic arthritis due to autoimmune diseases, fibromyalgia, etc.

As used herein, "effective amount" can refer to the amount of a disclosed compound or pharmaceutical composition provided herein that is sufficient to effect beneficial or desired biological, emotional, medical, or clinical response of a cell, tissue, system, animal, or human. An effective amount can be administered in one or more administrations, applications, or dosages. The term can also include within its scope amounts effective to enhance or restore to substantially normal physiological function or clinical response.

As used herein, the term "therapeutically effective amount" refers to an amount that is sufficient to achieve the desired therapeutic result or to have an effect on undesired symptoms. The specific therapeutically effective dose level for any particular subject will depend upon a variety of factors including the disorder or condition being treated and the severity of the disorder or condition; the specific composition employed; the age, body weight, general health, sex and diet of the subject; the time of administration; the time since eating solid food; drinking milk; the route of administration; the rate of excretion of the specific compound employed; the duration of the treatment; drugs used in combination or coincidental with the specific compound employed and like factors which may be well known in the medical arts. In the case of treating a particular disorder or condition, in some instances, the desired response can be inhibiting a worse progression of the disorder or condition, reducing the severity of the disorder or condition. The desired response to treatment of the disorder or condition also can be delaying the onset or even preventing the onset of the disorder or condition.

As used herein, the term "human" refers to any subject that is experiencing acute pain in need of pain relief. The age of the human is the age range suitable for administering naproxen sodium and famotidine. Thus, "human" as used herein includes adults and children of age that can take famotidine and naproxen sodium individually.

The unit oral dose compositions described herein treat acute pain while reducing the occurrence and/or severity of heartburn induced by the short-term use of OTC (not prescription-strength) naproxen sodium. The unit oral dose compositions described herein are not intended for the treatment of chronic pain. In another aspect, the unit oral dose composition further provides enhanced fever reduction and relief of fever-associated aches and pains in a human when compared to the administration to said human of the same dosage strength of said naproxen sodium in the absence of said famotidine.

The dosage of naproxen sodium and famotidine in the unit oral dose compositions described herein can vary. In one aspect, naproxen sodium is from about 100 mg to about 440 mg per unit oral dose composition, or about 100 mg, 110 mg, 120 mg, 132 mg, 137.5 mg, 140 mg, 147.4 mg, 150 mg, 160 mg, 165 mg, 178 mg, 180 mg, 200 mg, 220 mg, 240 mg, 250 mg, 260 mg, 280 mg, 300 mg, 320 mg, 330 mg, 340 mg, 360 mg, 380 mg, 400 mg, or 440 mg where any value can be a lower and upper endpoint of a range (e.g., about 200 mg to about 240 mg). In one aspect, naproxen sodium is about 220 mg per unit oral dose composition. In another aspect, naproxen sodium is about 110 mg per unit oral dose composition. In another aspect, naproxen sodium is about 148 mg per unit oral dose composition. In another aspect, naproxen sodium is about 165 mg per unit oral dose composition. In another aspect, naproxen sodium is about 178 mg per unit oral dose composition.

In one aspect, famotidine is from about 3 mg to about 20 mg per unit oral dose composition, or about 3 mg, 5 mg, 6.67 mg, 10 mg, 13.33 mg, 15 mg, 20 mg, where any value can be a lower and upper endpoint of a range (e.g., about 10 mg to about 20 mg). In one aspect, famotidine is about 3.33 mg, about 5 mg, about 6.67 mg, about 10 mg, or about 13.33 mg per unit oral dose composition.

In one aspect, naproxen sodium is from about 200 mg to about 300 mg per unit oral dose composition and famotidine is from about 3 mg to about 20 mg per unit oral dose composition. In another aspect, naproxen sodium is about 220 mg per unit oral dose composition and famotidine is from about 3 mg to about 10 mg per unit oral dose composition. In another aspect, naproxen sodium is about 220 mg per unit oral dose composition and famotidine is about 10 mg per unit oral dose composition. In another aspect, naproxen sodium is about 220 mg per unit oral dose composition and famotidine is about 13.33 mg per unit oral dose composition. In another aspect, naproxen sodium is from about 100 mg to about 300 mg per unit oral dose composition and famotidine is about 13.33 mg per unit oral dose composition. In another aspect, naproxen sodium is from about 200 mg to about 300 mg per unit oral dose composition and famotidine is about 13.3 mg per unit oral dose composition.

In another aspect, naproxen sodium is from about 110 mg to about 220 mg per unit oral dose composition and famotidine is about 10 mg to about 13.33 mg per unit oral dose composition. In another aspect, naproxen sodium is from about 178 mg to about 240 mg per unit oral dose composition and famotidine is about 10 mg to about 13.33 mg per unit oral dose composition. In another aspect, naproxen sodium is about 110 mg per unit oral dose composition and famotidine is about 10 mg or about 13.33 mg per unit oral dose composition.

In another aspect, naproxen sodium is from about 165 mg to about 220 mg per unit oral dose composition and famotidine is about 6.67 mg to about 13.3 mg per unit oral dose composition. In another aspect, naproxen sodium is about 165 mg per unit oral dose composition and famotidine is about 6.67 mg or about 10 mg per unit oral dose composition. In another aspect, naproxen sodium is about 165 mg per unit oral dose composition and famotidine is about 13.33 mg per unit oral dose composition. In another aspect, naproxen sodium is about 220 mg per unit oral dose composition and famotidine is about 13.33 mg per unit oral dose composition.

In other aspects, the unit oral dose compositions can include other bioactive agents. In one aspect, the unit oral dose composition further comprises a non-NSAID (non-steroidal anti-inflammatory drug) for relief of acute pain and reduction of fever. In one aspect, the unit oral dose composition further comprises a non-NSAID such as, for example, acetaminophen, preferably at a 5:3 or 3:2 ratio of the NSAID (e.g., naproxen sodium) to the non-NSAID (e.g., acetaminophen). In one aspect, the a non-NSAID is at a dosage of about 50 mg to about 500 mg, or about 50 mg, 60 mg, 65 mg, 66.67 mg, 70 mg, 75 mg, 80 mg, 85 mg, 88.67 mg, 90 mg, 100 mg, 125 mg, 133.34 mg, 150 mg, 160 mg, 166.67 mg, 200 mg, 225 mg, 250 mg, 300 mg, 325 mg, 375 mg, 400 mg, 450 mg, or 500 mg, where any value can be a lower and upper endpoint of a range (e.g., about 100 mg to about 200 mg or about 325 mg to about 500 mg). In another aspect, the non-NSAID is acetaminophen at a dosage of about 150 mg. In another aspect, the non-NSAID is acetaminophen at a dosage of about 250 mg. In another aspect, the non-NSAID is acetaminophen at a dosage of about 325 mg. In another aspect, naproxen sodium is about 220 mg combined with acetaminophen about 250 mg to about 325 mg per unit oral dose composition and famotidine is about 10 mg or about 13.33 mg per unit oral dose composition. In another aspect, naproxen sodium is about 220 mg combined with acetaminophen about 150 mg to about 325 mg per unit oral dose composition and famotidine is about 10 mg or about 13.33 mg per unit oral dose composition. In another aspect, naproxen sodium is about 220 mg combined with acetaminophen about 325 mg or about 500 mg per unit oral dose composition and famotidine is about 10 mg or about 13.33 mg per unit oral dose composition. In another aspect, naproxen sodium is about 250 mg combined with acetaminophen about 150 mg to about 325 mg per unit oral dose composition and famotidine is about 10 mg or about 13.33 mg per unit oral dose composition. In another aspect, naproxen sodium is about 250 mg combined with acetaminophen about 325 mg or about 500 mg per unit oral dose composition and famotidine is about 10 mg or about 13.33 mg per unit oral dose composition. In another aspect, naproxen sodium is about 200 mg combined with acetaminophen about 250 mg per unit oral dose composition and famotidine is about 10 mg or about 13.33 mg per unit oral dose composition. In another aspect, naproxen sodium is about 200 mg combined with acetaminophen about 325 mg or about 500 mg per unit oral dose composition and famotidine is about 10 mg to about 13.33 mg per unit oral dose composition. In another aspect, naproxen sodium is from about 150 mg to about 220 mg per unit oral dose composition combined with acetaminophen about 250 mg to about 500 mg per unit oral dose composition and famotidine is about 6.67 mg to about 13.33 mg per unit oral dose composition.

In one aspect, when the unit oral dose composition includes acetaminophen, the unit oral dose composition further provides enhanced and/or earlier pain reduction in the human when compared to the oral administration to the human of the same dosage strength of naproxen sodium in the absence of acetaminophen and famotidine. In one aspect, the unit oral dose composition with acetaminophen can provide enhanced fever reduction when compared to the oral administration to the human of the same dosage strength of naproxen sodium in the absence of acetaminophen and famotidine.

In another aspect, the unit oral dose composition (containing acetaminophen or not containing acetaminophen) further comprises a sleep aid for relief of occasional sleeplessness associated with minor aches and pains. In one aspect, the unit oral dose composition further comprises a sleep aid such as, for example, diphenhydramine HCl. In one aspect, the sleep aid is at a dosage of about 5 mg to about 50 mg, or about 5 mg, 10 mg, 12.5 mg, 15 mg, 20 mg, 25 mg, 30 mg, 35 mg, 40 mg, 45 mg, or 50 mg, where any value can be a lower and upper endpoint of a range (e.g., about 35 mg to about 40 mg). In another aspect, the sleep aid is diphenhydramine citrate at a dosage of about 12.5 mg.

In one aspect, when the unit oral dose composition includes diphenhydramine HCl or diphenhydramine citrate, the unit oral dose composition further provides enhanced and/or earlier pain reduction in the human when compared to the oral administration to the human of the same dosage strength of naproxen sodium in the absence of diphenhydramine, acetaminophen and famotidine. In one aspect, the unit oral dose composition with diphenhydramine HCl or diphenhydramine citrate can provide enhanced nighttime acute pain reduction for less awakening and increased duration of sleep, not disturbed by pain.

The unit oral dose compositions described herein can be formulated as pharmaceutical compositions for oral administration. In one aspect, the unit oral dose compositions can be in the form of solid dosage forms (i.e., unit oral solid dose composition) such as, for example, tablets, capsules, caplets, gelcaps, geltabs, pills, lozenges, chewable articles (e.g., a gummy), dissolvable strips (e.g., placement under the tongue), or any other suitable form for oral administration. In one aspect, the unit oral solid dose compositions can be oval-shaped or spherical-shaped forms such as tablets, capsules, caplets, gelcaps, geltabs, pills, lozenges, chewable articles (e.g., a gummy), etc. In another aspect, the unit oral dose compositions can be in the form of solid dosage forms which are on the exterior blue or blue-purple color, purple or violet color, deep blue or sea-blue, denim blue, or colonial blue, shades of blue/purple, or shades of blue, deep blue, blue/purple, sea-purple or violet color, denim blue or colonial blue with or without light brown speckles or dots.

In addition to naproxen sodium and famotidine, the unit oral dose compositions can include one or more pharmaceutically-acceptable carriers. As used herein, "pharmaceutically-acceptable carriers" means one or more of a pharmaceutically acceptable diluents, preservatives, antioxidants, solubilizers, emulsifiers, coloring agents, releasing agents, coating agents, sweetening, perfuming agents, and adjuvants. The disclosed pharmaceutical compositions can be conveniently presented in unit dosage form and prepared by any of the methods well known in the art of pharmacy and pharmaceutical sciences.

In one aspect, the unit oral dose compositions can be formulated with a flavoring agent. The flavoring agent can improve the desirable characteristics of taste, texture, and overall palatability of the unit oral dose compositions. The flavoring agent can be formulated with the unit oral dose composition in a number of different ways. In one aspect, the flavoring agent is admixed with naproxen sodium and/or famotidine along with one or more pharmaceutically acceptable carriers. In another aspect, the unit oral dose composition is spray-coated with a very thin film of the flavoring agent. Examples of flavoring agents useful herein include, but are not limited to, almond oil, vanillin, menthol, I-menthol, peppermint spirit, peppermint oil (liquid or solid state), or any combination thereof.

The unit oral dose compositions can include one or more pharmaceutical excipients and/or additives. Non-limiting examples of suitable excipients and additives include magnesium stearate, titanium dioxide, red iron oxide, yellow iron oxide, gelatin, natural sugars such as raw sugar or lactose, non-sugar sweeteners (e.g., aspartame, acesulfame potassium, luo han guo (monk) fruit extract, neotame, saccharin, *stevia*, sucralose and advantame), lecithin, pectin, starches (for example corn starch or amylose), dextran, polyvinyl pyrrolidone, polyvinyl acetate, gum arabic, alginic acid, tylose, talcum, lycopodium, silica gel (for example colloidal), cellulose, cellulose derivatives (for example cellulose ethers in which the cellulose hydroxy groups are partially etherified with lower saturated aliphatic alcohols and/or lower saturated, aliphatic oxyalcohols, for example methyl oxypropyl cellulose, methyl cellulose, hydroxypropyl methyl cellulose, hydroxypropyl methyl cellulose phthalate, microcrystalline cellulose), fatty acids as well as magnesium, calcium or aluminum salts of fatty acids with 12 to 22 carbon atoms, in particular saturated (for example stearates), emulsifiers, oils and fats, in particular vegetable (for example, peanut oil, castor oil, olive oil, sesame oil, cottonseed oil, corn oil, wheat germ oil, sunflower seed oil, cod liver oil, in each case also optionally hydrated); glycerol esters and polyglycerol esters of saturated fatty acids $C_{12}H_{24}O_2$ to $C_{18}H_{36}O_2$ and their mixtures, it being possible for the glycerol hydroxy groups to be totally or also only partly esterified (for example mono-, di- and triglycerides); pharmaceutically acceptable mono- or multivalent alcohols and polyglycols such as polyethylene glycol and derivatives thereof, esters of aliphatic saturated or unsaturated fatty acids (2 to 22 carbon atoms, in particular 10-18 carbon atoms) with monovalent aliphatic alcohols (1 to 20 carbon atoms) or multivalent alcohols such as glycols, glycerol, diethylene glycol, pentacrythritol, sorbitol, mannitol and the like, which may optionally also be etherified, esters of citric acid with primary alcohols, acetic acid, urea, benzyl benzoate, dioxolanes, glyceroformals, tetrahydrofurfuryl alcohol, polyglycol ethers with C1-C12-alcohols, dimethylacetamide, lactamides, and the like.

Other auxiliary substances useful in preparing the unit oral dose compositions are those which cause disintegration (so-called disintegrants), such as: cross-linked polyvinyl pyrrolidone, sodium carboxymethyl starch, sodium carboxymethyl cellulose or microcrystalline cellulose. Conventional coating substances may also be used to produce the oral dosage form. Those that may for example be considered are: polymerizates as well as copolymerizates of acrylic acid and/or methacrylic acid and/or their esters; copolymerizates of acrylic and methacrylic acid esters with a lower ammonium group content (for example sold under the trademark EUDRAGIT® RS), copolymerizates of acrylic and methacrylic acid esters and trimethyl ammonium methacrylate (for example sold under the trademark EUDRAGIT® RL); polyvinyl acetate; fats, oils, waxes, carnauba wax, fatty alcohols; hydroxypropyl methyl cellulose phthalate or acetate succinate; cellulose acetate phthalate, starch acetate phthalate as well as polyvinyl acetate phthalate, carboxy methyl cellulose; methyl cellulose phthalate, methyl cellulose succinate, -phthalate succinate as well as methyl cellulose phthalic acid half ester; zein; ethyl cellulose as well as ethyl cellulose succinate; shellac, gluten; ethylcarboxyethyl cellulose; ethacrylate-maleic acid anhydride copolymer; maleic acid anhydride-vinyl methyl ether copolymer; styrol-maleic acid copolymerizate; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; cellulose acetate succinate; polyarginine.

Plasticizing agents that may be considered as coating substances with the unit oral dose compositions citric and tartaric acid esters (acetyl-triethyl citrate, acetyl tributylcitrate, triethyl-citrate); glycerol and glycerol esters (glycerol diacetate, -triacetate, acetylated monoglycerides, castor oil); phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and diburylsebacate, dibutylsuccinate, dibutyltartrate; diethylene glycol dipropionate; ethyleneglycol diacetate, -dibutyrate, -dipropionate; tributyl phosphate, tributyrin; polyethylene glycol sorbitan monooleate (polysorbates such as polysorbate 50); sorbitan monooleate.

Moreover, suitable binders, lubricants, disintegrating agents, coloring agents, flavoring agents, flow-inducing agents, and melting agents may be included as carriers. The pharmaceutical carrier employed can be, for example, a solid, liquid, or gas. Examples of solid carriers include, but are not limited to, lactose, terra alba, sucrose, glucose, methylcellulose, dicalcium phosphate, calcium sulfate, mannitol, sorbitol talc, starch, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In various aspects, a binder can include, for example, starch, gelatin, natural sugars such as glucose or betalactose, corn sweeteners, hypromellose, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium acetate, sodium chloride, and the like. In a further aspect, a disintegrator can include, for example, starch, methyl cellulose, sodium starch glycolate, agar, bentonite, xanthan gum, and the like.

In certain aspects, the unit oral dose compositions are formulated such that famotidine is released prior to (at a greater rate than) naproxen sodium. In one aspect, a disintegrant or diluent can be admixed with famotidine followed by formulation with naproxen sodium to produce the unit oral dose composition. In another aspect, the unit oral dose composition can include different disintegrants or diluents in order to release famotidine first followed by naproxen sodium (e.g, famotidine is admixed with a first disintegrant and naproxen sodium is admixed with a second disintegrant). In another aspect, when the same disintegrant is used, the amount of disintegrant admixed with famotidine can be greater than the amount of disintegrant admixed with naproxen sodium.

In one aspect, the unit oral dose composition includes microparticles and/or nanoparticles of famotidine. In certain aspects, the unit oral dose composition is composed of a first population of microparticles composed of famotidine and a second population of microparticles composed of naproxen sodium. In one aspect, the particle size of the first population of microparticles is different than the particle size of the second population of microparticles. In another aspect, the first population of microparticles is composed of a different material than the second population of microparticles. By varying the particle size and composition of the first and second population of microparticles, it is possible to vary the dissolution rate of each population of microparticles.

In another aspect, the unit oral dose composition includes microparticles and/or nanoparticles of famotidine. In certain aspects, the unit oral dose composition is composed of a first population of microparticles composed of famotidine, a second population of microparticles composed of naproxen sodium, and a third population of microparticles composed of acetaminophen. In one aspect, the particle size of the first population of microparticles is different than the particle size of the second population of microparticles. In another aspect, the particle size of the second population of microparticles is different than the particle size of the third populations of microparticles. In another aspect, the first population of microparticles is composed of a different material than the second population of microparticles. In another aspect, the second population of microparticles is composed of a different material than the third population of microparticles. By varying the particle size and composition of the first, second and third population of microparticles, it is possible to vary the dissolution rate of each population of microparticles. In one aspect, the microparticles can be manufactured by traditional techniques based on friction such as, for example, milling or grinding (e.g., spiral jet milling, fluid bed jet milling). In another aspect, the microparticles can be manufactured by precipitation from saturated or super saturated solutions, spray drying, or in situ micronization (Hovione) methods. In other aspects, supercritical fluids can be used to produce the micronized particles useful herein. Techniques such as, for example, Rapid Expansion of Supercritical Solutions (RESS), Supercritical Anti-Solvent (SAS), Particles from Gas Saturated Solutions (PGSS) use supercritical fluids to produce micronized particles. US Publication Nos. 2021/0106511 and 2021/0060268, which are incorporated by reference in their entireties, provides non-limiting techniques for producing microparticles for the oral delivery of therapeutic agents. In one aspect, microparticles of famotidine can have an average particle diameter of from about 1 μm to about 1,000 μm, or about 1 μm, 10 μm, 20 μm, 30 μm, 40 μm, 50 μm, 60 μm, 70 μm, 80 μm, 90 μm, 100 μm, 150 μm, 200 μm, 250 μm, 300 μm, 350 μm, 400 μm, 450 μm, 500 μm, 500 μm, 550 μm, 600 µm, 650 µm, 700 µm, 750 µm, 800 µm, 850 µm, 900 µm, 950 µm, or 1,000 µm, where any value can be a lower and upper endpoint of a range (e.g., 10 µm to 100 µm).

In other aspects, the unit oral dose compositions can be formulated with nanoparticles to produce rapidly dissolving oral formulations. In one aspect, polymers (e.g., polysaccharides such as amylopectin, starch, glycogen, cellulose, dextrin, chitin, alpha glucan, beta glucan, and combinations thereof) or inorganic materials (e.g., inert silica) can be admixed with famotidine and naproxen sodium followed by the production of nanoparticles using techniques known in the art such as, for example, ionotropc gelation or spray-drying. US Publication No. 2015/0147399, which is incorporated by reference in its entirety, provides non-limiting techniques for producing nanoparticles for the oral delivery of therapeutic agents.

In one aspect, nanoparticles of famotidine can have an average particle diameter of from about 1 nm to about 1,000 nm, or about 1 nm, 10 nm, 20 nm, 30 nm, 40 nm, 50 nm, 60 nm, 70 nm, 80 nm, 90 nm, 100 nm, 150 nm, 200 nm, 250 nm, 300 nm, 350 nm, 400 nm, 450 nm, 500 nm, 500 nm, 550 nm, 600 nm, 650 nm, 700 nm, 750 nm, 800 nm, 850 nm, 900 nm, 950 nm, or 1,000 nm, where any value can be a lower and upper endpoint of a range (e.g., 10 nm to 100 nm).

In certain aspects, the unit oral dose composition is composed a first population of nanoparticles composed of famotidine and a second population of nanoparticles composed of naproxen sodium. In one aspect, the particle size of the first population of nanoparticles is different than the particle size of the second population of nanoparticles. In another aspect, the first population of nanoparticles is composed of a different material than the second population of nanoparticles. By varying the particle size and composition of the first and second population of nanoparticles, it is possible to vary the dissolution rate of each population of nanoparticles.

In certain aspects, the unit oral dose composition is composed of a first population of nanoparticles composed of famotidine, a second population of nanoparticles composed of naproxen sodium, and a third population of nanoparticles composed of acetaminophen. In one aspect, the particle size of the first population of nanoparticles is different than the particle size of the second population of nanoparticles. In another aspect, the particle size of the second population of nanoparticles is different than the particle size of the third population of nanoparticles. In another aspect, the first population of nanoparticles is composed of a different material than the second population of nanoparticles. In another aspect, the second population of nanoparticles is composed of a different material than the third population of nanoparticles. By varying the particle size and composition of the first, second and third population of nanoparticles, it is possible to vary the dissolution rate of each population of nanoparticles.

In one aspect, the unit oral dose composition is composed a first population of nanoparticles composed of (1) famotidine with inert ingredients such as, for example, hydroxypropyl cellulose, hypromellose, iron oxides, magnesium stearate, microcrystalline cellulose, corn starch, talc, titanium dioxide, and carnauba wax, and any combination thereof; (2) a second population of nanoparticles composed of naproxen sodium with inert ingredients such as, for example, gelatin, glycerin, hypromellose, lactic acid, mannitol, polyethylene glycol, povidone, propylene glycol, sorbitan, sorbitol, titanium dioxide, or any combination thereof; and (3) a third population of nanoparticles composed of acetaminophen with inert ingredients such as, for example, hypromellose, magnesium stearate, starch, microcrystalline cellulose, propylene glycol, titanium dioxide polysorbate 80, povidone, stearic acid, titanium dioxide, carnauba wax, or any combination thereof.

In one aspect, the average particle size of the naproxen sodium is greater than average particle size of the famotidine. In one aspect, the average particle size of the naproxen sodium is 1.5, 2, 2.5, 3, 3, 3.5, 4, 4.5, 5, 6, 7, 8, 9, or 10 times greater than the average particle size of famotidine.

In another aspect, the average particle size of the naproxen sodium is greater than average particle size of the acetaminophen. In one aspect, the average particle size of the naproxen sodium is 1.5, 2, 2.5, 3, 3, 3.5, 4, 4.5, 5, 6, 7, 8, 9, or 10 times greater than the average particle size of acetaminophen.

In one aspect, a tablet containing famotidine and naproxen sodium can be prepared by compression or molding, optionally with one or more accessory ingredients or adjuvants. Compressed tablets can be prepared by compression or pressing machines, where the components can be in a free-flowing form such as powder or granules and optionally mixed with a binder, lubricant, inert diluent, surface active or dispersing agent. Molded tablets can be made by molding in a suitable machine, a mixture of the powdered compound moistened with an inert liquid diluent. In one aspect, the tablet includes microparticles and/or nanoparticles of famotidine.

In another aspect, a bi-layer tablet with a first layer composed of famotidine and a second layer composed of naproxen sodium can be formulated as the unit oral dose composition. In one aspect, the unit oral dose composition is a bi-layer tablet composed of (1) a first layer composed of famotidine with inert ingredients such as, for example, hydroxypropyl cellulose, hypromellose, iron oxides, magnesium stearate, microcrystalline cellulose, corn starch, talc, titanium dioxide, and carnauba wax, and any combination thereof and (2) a second layer composed of naproxen sodium with inert ingredients such as, for example, gelatin, glycerin, hypromellose, lactic acid, mannitol, polyethylene glycol, povidone, propylene glycol, sorbitan, sorbitol, titanium dioxide, or any combination thereof.

In another aspect, a bi-layer tablet with a first layer composed of famotidine and acetaminophen and a second layer composed of naproxen sodium can be formulated as the unit oral dose composition. In one aspect, the unit oral dose composition is a bi-layer tablet composed of (1) a first layer composed of famotidine and acetaminophen with inert ingredients such as, for example, hydroxypropyl cellulose, hypromellose, iron oxides, magnesium stearate, microcrystalline cellulose, corn starch, talc, titanium dioxide, and carnauba wax, and any combination thereof and (2) a second layer composed of naproxen sodium with inert ingredients such as, for example, gelatin, glycerin, hypromellose, lactic acid, mannitol, polyethylene glycol, povidone, propylene glycol, sorbitan, sorbitol, titanium dioxide, or any combination thereof.

In another aspect, the unit oral dose composition can be formulated as a solid dose spherical- or oval-shaped form, where the core of the solid dose form is composed of naproxen sodium surrounded by an outer layer of famotidine. In one aspect, the unit oral dose composition is composed of (1) a first layer composed of famotidine with inert ingredients such as, for example, hydroxypropyl cellulose, hypromellose, iron oxides, magnesium stearate, microcrystalline cellulose, corn starch, talc, titanium dioxide, and carnauba wax, and any combination thereof surrounding a core composed of (2) naproxen sodium with inert ingredients such as, for example, gelatin, glycerin, hypromellose, lactic acid, mannitol, polyethylene glycol, povidone, propylene glycol, sorbitan, sorbitol, titanium dioxide, or any combination thereof.

In another aspect, the unit oral dose composition can be formulated as a solid dose spherical- or oval-shaped form, where the core of the solid dose form is composed of naproxen sodium surrounded by an outer layer of famotidine and acetaminophen. In one aspect, the unit oral dose composition is composed of (1) a first layer composed of famotidine and acetaminophen with inert ingredients such as, for example, hydroxypropyl cellulose, hypromellose, iron oxides, magnesium stearate, microcrystalline cellulose, corn starch, talc, titanium dioxide, and carnauba wax, and any combination thereof surrounding a core composed of (2) naproxen sodium with inert ingredients such as, for example, gelatin, glycerin, hypromellose, lactic acid, mannitol, polyethylene glycol, povidone, propylene glycol, sorbitan, sorbitol, titanium dioxide, or any combination thereof.

In one preferred aspect, the unit oral dose composition comprises a solid dosage form, wherein the core of the solid dosage form comprises naproxen sodium surrounded by an outer layer of famotidine microparticles. The naproxen sodium core may vary in shape and may be, for example, round, ovoid, oblong, convex, cylindrical (e.g., disk shaped) or any other suitable geometric shape, for example rectilinear. Preferably the tablet has a disk, spherical, rhomboidal or oval-shape that is ovoid-contoured like a flattened disk or torpedo. The edges of the tablets may be beveled or rounded. The tablet may also be shaped as a caplet (capsule form tablet). The tablets may be scored, embossed or engraved. In one embodiment, the core does not have an internal hole extending all or part-way through the pill.

The famotidine layer can be applied to the naproxen sodium core using techniques known in the art. In one aspect, the famotidine is applied to the naproxen sodium core by compression or spray coating. In one aspect, the methods disclosed in US Publication No. 2019/0307702, which is incorporated by reference in its entirety, provides non-limiting techniques for producing multiparticulates comprising a melt-congeal core surrounded by a solid amorphous dispersion layer comprising a drug and a polymer. In one aspect, the famotidine layer can have a thickness of from about 10 µm to about 500 µm, or about 10 µm, 20 µm, 30 µm, 40 µm, 50 µm, 60 µm, 70 µm, 80 µm, 90 µm, 100 µm, 150 µm, 200 µm, 250 µm, 300 µm, 350 µm, 400 µm, 450 µm, 500 µm, or 500 µm, where any value can be a lower and upper endpoint of a range (e.g., 10 µm to 100 µm).

In another aspect, the unit oral dose composition comprises a solid dosage form, wherein the core of the solid dosage form comprises naproxen sodium surrounded by an outer layer of famotidine microparticles and acetaminophen particles. The naproxen sodium core may vary in shape and may be, for example, round, ovoid, oblong, convex, cylindrical (e.g., disk shaped) or any other suitable geometric shape, for example rectilinear. Preferably the tablet has a disk, spherical, rhomboidal, or oval-shape that is ovoid-contoured like a flattened disk or torpedo. The edges of the tablets may be beveled or rounded. The tablet may also be shaped as a caplet (capsule form tablet). The tablets may be scored, embossed or engraved. In one embodiment, the core does not have an internal hole extending all or part-way through the pill.

The famotidine and acetaminophen layer can be applied to the naproxen sodium core using techniques known in the art. In one aspect, the famotidine and acetaminophen are applied to the naproxen sodium core by compression or spray coating. In one aspect, the methods disclosed in US Publication No. 2019/0307702, which is incorporated by reference in its entirety, provides non-limiting techniques for producing multi-particulates comprising a melt-congeal core surrounded by a solid amorphous dispersion layer comprising a drug and a polymer. In one aspect, the famotidine and acetaminophen layer can have a thickness of from about 10 µm to about 500 µm, or about 10 µm, 20 µm, 30 µm, 40 µm, 50 µm, 60 µm, 70 µm, 80 µm, 90 µm, 100 µm, 150 µm, 200 µm, 250 µm, 300 µm, 350 µm, 400 µm, 450 µm, 500 µm, or 500 µm, where any value can be a lower and upper endpoint of a range (e.g., 10 µm to 100 µm). In another aspect, the famotidine is applied to the naproxen sodium core by compression or spray coating, and the acetaminophen is applied to the famotidine layer by compression or spray coating. In one aspect, the famotidine and acetaminophen layers can have a thickness of from about 10 µm to about 500 µm, or about 10 µm, 20 µm, 30 µm, 40 µm, 50 µm, 60 µm, 70 µm, 80 µm, 90 µm, 100 µm, 150 µm, 200 µm, 250 µm, 300 µm, 350 µm, 400 µm, 450 µm, 500 µm, or 500 µm, where any value can be a lower and upper endpoint of a range (e.g., 10 µm to 100 µm).

In one aspect, the unit oral dose compositions optionally include a release-delaying agent. In another aspect, the unit oral dose compositions do not include a release-delaying agent. Two common classes of release-delaying agents are "enteric" (i.e., allowing release within a specific milieu of the gastro-intestinal tract) and "fixed-time" (i.e., allowing release after a pre time period after administration, regardless of gastro-intestinal milieu).

Enteric release-delaying agents allow release at a certain pH or in the presence of degradative enzymes that are characteristically present in specific locations of the GI tract where release is desired. The enteric material typically remains insoluble at gastric pH, then allows for release of the active ingredient in the higher pH environment of the downstream gastrointestinal tract (e.g., often the duodenum, or sometimes the colon). The enteric material includes enzymatically degradable polymers that are degraded by bacterial enzymes present in the lower gastrointestinal tract, particularly in the colon.

Materials used for enteric release formulations include cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the trademark EUDRAGIT® (Rohm Pharma; Westerstadt, Germany), including EUDRAGIT® L30D-55 and L100-55 (soluble at pH 5.5 and above), EUDRAGIT® L-100 (soluble at pH 6.0 and above), EUDRAGIT® S (soluble at pH 7.0 and above, as a result of a higher degree of esterification), and EUDRAGIT® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. A preferred coating agent is methacrylic acid copolymer NF (commonly sold under the trademark EUDRAGIT® L100-55).

The release-delaying agent allows the release of drug after a predetermined lag period after the composition is brought into contact with body fluids ("fixed-time delayed release"). Unlike enteric release, fixed-time release is not particularly affected by environmental pH or enzymes.

A large number of fixed-time release-delaying agents are known to those of ordinary skill in the art. Exemplary materials which are useful for making the time-release coating include, by way of example, water soluble polysaccharide gums such as carrageenan, fucoidan, gum ghatti, tragacanth, arabinogalactan, pectin, and xanthan; water-soluble salts of polysaccharide gums such as sodium alginate, sodium tragacanthin, and sodium gum ghattate; water-soluble hydroxyalkylcellulose wherein the alkyl member is straight or branched of 1 to 7 carbons such as hydroxymethylcellulose, hydroxyethylcellulose, and hydroxypropylcellulose; synthetic water-soluble cellulose-based lamina formers such as methyl cellulose and its hydroxyalkyl methylcellulose cellulose derivatives such as a member selected from the group consisting of hydroxyethyl methylcellulose, hydroxypropyl methylcellulose, and hydroxybutyl methylcellulose; other cellulose polymers such as sodium carboxymethylcellulose, cellulose acetate, cellulose acetate butyrate and ethyl cellulose; and other materials known to those of ordinary skill in the art. Other film-forming materials that can be used for this purpose include poly(vinylpyrrolidone), polyvinylalcohol, polyethylene oxide, a blend of gelatin and polyvinyl-pyrrolidone, gelatin, glucose, saccharides, povidone, copovidone, poly(vinylpyrrolidone)-poly(vinyl acetate) copolymer. Other materials which can be used in the time-release coating include methacrylic resins commonly sold under the trademarks EUDRAGIT® NE, RL and RS, hydroxypropylcellulose, microcrystalline cellulose (MCC, commonly sold under the trademark AVICEL® from FMC Corp.), poly(ethylene-vinyl acetate) (60:40) copolymer (EVAC from Aldrich Chemical Co.), 2-hydroxyethylmethacrylate (HEMA), methyl methacrylate (MMA), and calcium pectinate can be included. Substances that are used as excipients within the pharmaceutical industry can also act as release-delaying agents.

Common types of fixed-time release dosage forms include erodible formulations, formulations that undergo osmotic rupture, or unit dosage form that use any combination of mechanisms for delayed-burst release.

Fixed-time release-delaying agents (RDAs) can optionally achieve a delayed-burst release by osmotic rupture. Examples of such RDAs include swelling agents, osmogens, binders, lubricants, film formers, pore formers, coating polymers and/or plasticizers.

Osmotic rupture is achieved by a delayed-burst release component, which includes a coated unit dosage form that contains the drug and a swelling agent within the semipermeable coating (e.g., ethylcellulose). The coating weight (thickness) of the semipermeable coating can be selected to delay release by osmotic rupture for a desired period. To identify the correct coating weight for a particular delay, unit dosage forms with a range of coating weights can be tested via in vitro dissolution to determine the burst time. Based on these results, a coating weight that achieves the desired lag period would be selected. In addition, the amount and/or ratio of coating strength modifier (e.g., talc) in the coating can be adjusted as well. Other formulation variables that can also be adjusted to obtain the desired release by osmotic rupture include the amount of sweller layer and sweller and/or fillers in the formulation. In the case of rupturing tablets, the amount of sweller would be selected to achieve the target release, while still providing the tablet with sufficient compressibility and acceptably low friability to be manufacturable.

One or more "diffusion regulators" can control the permeation of bodily fluids and delay the release of a bioactive. Exemplary diffusion regulators include hydrophilic polymers, electrolytes, proteins, peptides, amino acids and others known to those of ordinary skill in the pharmaceutical sciences. In an example, the fixed-time release-delaying agent comprises a coating that permits release of drug after a fixed period. The thickness of the coating can affect the time required for penetration of fluids into the formulation. For example, a diffusion controlling time release coating that provides release after a fixed delay period of about 0.5-2.5 hours could be about 200-1000 microns thick, and one that provides a release after a fixed delay period of about 2.5-5.0 hours could be about 1000-3000 microns thick.

Examples of osmotic rupturing multiparticulates are demonstrated in the literature (See, e.g., Dashevsky, et al, International Journal of Pharmaceutics, 318, (2006) 124-131; Mohamed, et al, Drug Development and Industrial Pharmacy, 33 (2007) 113-119; U.S. Pat. No. 4,871,549; Ueda, S., et al, Journal of Drug Targeting, 2 (1994) 35-44; Ueda, S., et al, Chemical Pharmaceutical Bulletin, 42(2), (1994) 359-363; Ueda, S., et al, Chemical Pharmaceutical Bulletin, 42(2), (1994) 364-367). Examples of osmotic rupturing tablets are demonstrated in the literature (U.S. Pat. No. 4,871,549; Theeuwes, F., Journal of Pharmaceutical Sciences, Vol. 64, No. 12, (1975) 1987-1991; Sungthongjeen, S., et al, Journal of Controlled Release, 95, (2004) 147-159).

Erodible formulations provide another example of fixed-time release formulations. The release delay from an erodible coated tablet can be adjusted by those of ordinary skill in the art by regulating the erodible layer coating weight. To identify the correct coating weight, tablets over a range of coating weights can be tested via in vitro dissolution (and/or erosion) to determine the burst time. Other formulation variables that may affect performance are the selection of the coating layer polymer type and viscosity. Examples of erodible coated tablets are demonstrated in the literature (Sangalli, M. E., et. al., Journal of Controlled Release, 73 (2001) 103-110; Gazzaniga, A., et. al., International Journal of Pharmaceutics, 108 (1994) 77-83).

The unit oral dose composition can include one or more "erosion regulators" that control the erosion rate of the coating. Any material or combination of materials may serve as an erosion regulator. Exemplary erosion and/or diffusion regulators include hydrophilic polymers, electrolytes, proteins, peptides, amino acids and others known to those of ordinary skill in the pharmaceutical sciences. The thickness of the coating can affect the time required for erosion of the coating. For example, an erodible time-release coating that provides release after a fixed period of about 0.5-2.5 hours could be about 100-2,000 microns thick, and one that provides release after a fixed delay period of about 2.5-5.0 hours could be about 2,000-5,000 microns thick.

The unit oral dose compositions may include a colorant such as titanium dioxide, iron oxide-based colorants or others. In one aspect, the outer surface of the unit oral dose composition is coated with colorant having a blue hue (e.g., dark blue, cobalt blue, exterior blue or blue-purple color, purple or violet color, deep blue or sea-blue, denim blue or colonial blue, or shades of blue, deep blue, blue/purple, sea-purple or violet color, denim blue or colonial blue).

In one embodiment the barrier layer comprises a non-toxic edible polymer, edible pigment particles, an edible polymer plasticizer, and a surfactant. Materials include, for example and not limitation, materials described in U.S. Pat. No. 4,543,370 (Colorcon), incorporated herein by reference. Exemplary barrier layers include that commonly sold under the trademark OPADRY®, which is available from Colorcon (West Point PA USA); that commonly sold under the trademark OPADRY® II which is available from Colorcon (West Point PA USA) and comprises hydroxypropyl methylcellulose (HPMC), titanium dioxide, plasticizer and other components;

By using sensitive methods to test the dissolution of the oral dose composition from solid form into solution at a specified time, percentage differences in the rates of dissolution between different compositions can be determined. In one aspect, the unit oral dose composition of the present invention is formulated such that, regardless of the presence or absence of acetaminophen in the unit oral dose composition, the dissolution rate of famotidine in the unit oral dose composition at a specified time is greater than the dissolution rate of naproxen sodium in the unit oral dose composition at the same specified time. In one aspect, the dissolution rate of famotidine is from about 10% to about 200% greater over a specified period of time than that of only famotidine at the same dosage in the unit dose composition over the same specified period of time during the initial 45 minutes after drug administration (e.g., 0 to 5 minutes, 0 to 10 minutes, 0 to 15 minutes, 0 to 20 minutes, 0 to 25 minutes, 0 to 30 minutes, 0 to 45 minutes). In another aspect, the dissolution rate of famotidine is from about 10%, about 20%, about 30%, about 40%, about 50%, about 60%, about 70%, about 80%, about 90%, about 100%, about 110%, about 120%, about 130%, about 140%, about 150%, about 160%, about 170%, about 180%, about 190%, or about 200% over a specified period of time greater than that of only famotidine at the same dosage in the unit dose composition over the same specified period of time (e.g., 0 to 5 minutes, 0 to 10 minutes, 0 to 15 minutes, 0 to 20 minutes, 0 to 30 minutes, 0 to 45 minutes), where any value can be a lower and upper endpoint of a range (e.g., about 50% to about 150%).

In one aspect, the dissolution rate of famotidine is from about 10% to about 200% greater over a specified period of time than the dissolution rate of naproxen sodium in the unit dose composition over the same specified period of time during the initial 45 minutes after drug administration (e.g., 0 to 5 minutes, 0 to 10 minutes, 0 to 15 minutes, 0 to 20 minutes, 0 to 25 minutes, 0 to 30 minutes, 0 to 45 minutes). In another aspect, the dissolution rate of famotidine is from about 10%, about 20%, about 30%, about 40%, about 50%, about 60%, about 70%, about 80%, about 90%, about 100%, about 110%, about 120%, about 130%, about 140%, about 150%, about 160%, about 170%, about 180%, about 190%, or about 200% over a specified period of time greater than that of naproxen sodium in the unit dose composition over the same specified period of time (e.g., 0 to 5 minutes, 0 to 10 minutes, 0 to 15 minutes, 0 to 20 minutes, 0 to 30 minutes, 0 to 45 minutes), where any value can be a lower and upper endpoint of a range (e.g., about 50% to about 150%).

In one aspect, the dissolution rate of famotidine in the unit oral dose composition in said human is measured over a specified period of time (e.g., within the initial 15 to 45 minutes). In another aspect, the dissolution rate of famotidine in the unit oral dose composition in said human measured at a specified time (for example, at about 5 minutes or at about 10 minutes) is greater than the dissolution rate of naproxen sodium in the unit oral dose composition in said human because naproxen sodium is non-detectable or very low at the same specified time.

In one aspect, the famotidine in the unit oral dose composition has a dissolution rate that is about 10% to about 30% greater than the dissolution rate of naproxen sodium at about 5 minutes, at about 10 minutes, at about 15 minutes, at about 20 minutes, at about 25 minutes, at about 30 minutes or at about 45 minutes after administration of the unit oral dose composition to the human. In another aspect, for example, about 50% of the famotidine is released from the unit oral dose composition about 15 minutes after administration of said unit oral dose composition in said human and about 25% of the naproxen sodium is released from the unit oral dose composition about 15 minutes after administration of said unit oral dose composition in said human, indicating that about 25% more famotidine (i.e., 50%-25%) is dissolved in said human than naproxen sodium at 15 minutes in said human. Since 50% dissolution is 2 times the 25% absolute difference in dissolution rates, the dissolution of famotidine is 2 times greater than the dissolution of naproxen sodium at 15 minutes. In another aspect, about 80% of the famotidine is released from the unit oral dose composition about 30 minutes after administration of said unit oral dose composition in said human and about 40% of the naproxen sodium is released from the unit oral dose composition about 30 minutes after administration of said unit oral dose composition in said human, indicating that about 40% more famotidine (i.e., 80%-40%) is dissolved in said human than naproxen sodium at 30 minutes in said human. Since 80% dissolution is 2 times the 40% absolute difference in dissolution rates, the dissolution of famotidine is 2 times greater than the dissolution of naproxen sodium at 30 minutes.

In one aspect, the famotidine in the unit oral dose composition has a dissolution rate at about 10 minutes after administration of said unit oral dose composition to said human that is about 5 minutes to less than 10 minutes earlier than the time required for naproxen sodium in said unit oral dose composition to achieve the same dissolution rate after administration of the unit oral dose composition to the human. For example, if 50% of the famotidine is released from the unit oral dose composition 10 minutes after administration of said unit oral dose composition, and 50% of the naproxen sodium is released from the unit oral dose composition at about 20 minutes after administration of said unit oral dose composition, then famotidine is released about 10 minutes earlier than naproxen sodium (i.e., famotidine is dissolved earlier than naproxen sodium from the unit oral dose composition).

In one aspect, the famotidine in the unit oral dose composition has a dissolution rate at about 15 minutes after administration of said unit oral dose composition to said human that is about 5 minutes to about 10 minutes earlier than the time required for naproxen sodium in said unit oral dose composition to achieve the same dissolution rate after administration of the unit oral dose composition to the human (i.e., famotidine is dissolved earlier than naproxen sodium).

In another aspect, the famotidine in the unit oral dose composition has a dissolution rate at about 20 minutes after administration of said unit oral dose composition to said human that is about 5 minutes to about 15 minutes earlier than the time required for naproxen sodium in said unit oral dose composition to achieve the same dissolution rate after administration of the unit oral dose composition to the human (i.e., famotidine is dissolved earlier than naproxen sodium).

In another aspect, the famotidine in the unit oral dose composition has a dissolution rate at about 30 minutes after administration of said unit oral dose composition to said human that is about 5 minutes to about 25 minutes earlier than the time required for naproxen sodium in said unit oral dose composition to achieve the same dissolution rate after administration of the unit oral dose composition to the human (i.e., famotidine is dissolved earlier than naproxen sodium).

In another aspect, the famotidine in the unit oral dose composition has a dissolution rate at about 45 minutes after administration of said unit oral dose composition to said human that is about 5 minutes to about 40 minutes earlier than the time required for naproxen sodium in said unit oral dose composition to achieve the same dissolution rate after administration of the unit oral dose composition to the human (i.e., famotidine is dissolved earlier than naproxen sodium).

The dissolution rate can be determined using in vitro techniques known in the art. The specific dissolution technique employed is determined by the dosage form characteristics and the intended route of administration. For solid dosage forms, industry standard dissolution testing methodologies include the United States Pharmacopoeia (USP) Apparatus 1 (basket) and the USP Apparatus 2 (paddle). Immediate-release, modified-release and extended release tablets are usually tested in classical dissolution baths with USP 2 paddles. Floating capsules and tablets generally use USP 1 baskets. Other dissolution techniques and equipment include USP 3 (reciprocating cylinders), USP 4 (flow-through-cell), USP 5 (paddle-over-disk), USP 6 (cylinder) and USP 7 (reciprocating holders). The development of a dissolution procedure involves selecting the dissolution media, apparatus type and hydrodynamics (agitation rate) appropriate for the product.

In one aspect, an in vitro dissolution assay is carried out by placing the unit oral dose composition in a known volume of dissolution medium in a container with a suitable stirring device (e.g., a rotating basket or paddle of specified size and shape). Samples of the medium are withdrawn at various times over 60 minutes and analyzed for dissolved active substance to determine the rate of dissolution. In one aspect, the dissolution method increases the number of units tested per assay (up to 48 tablets) and samples are obtained at more frequent intervals (at 5-minute intervals over 60 minutes) to improve the sensitivity and accuracy of the dissolution assay. Dissolution may be measured as described for naproxen sodium in the USP or, alternatively, as described for famotidine in the USP. For example, the unit dose composition is placed in a vessel of a United States Pharmacopeia dissolution apparatus II (Paddles) containing 900 ml dissolution medium at 37° C. The paddle speed is 50 RPM. Independent measurements are made for at least three (3) unit dose compositions. In one suitable in vitro assay, dissolution is measured using a neutral dissolution medium such as 50 mM potassium phosphate buffer, pH 7.2 ("neutral conditions"). In another aspect, the dissolution rate is measured in a Type II dissolution apparatus (paddles) according to U.S. Pharmacopoeia 29 at 37° C. in 50 mM potassium phosphate buffer, pH 7.2 at 50 rotations per minute.

Described herein are unit oral dose compositions for preventing the occurrence of heartburn and/or reducing the severity of heartburn in a human when taking naproxen sodium for the treatment of acute pain. The unit oral dose compositions described herein are particularly useful to humans with a history indicating they experience heartburn when taking over-the-counter (OTC) NSAIDs such as naproxen sodium, ibuprofen and aspirin (acetylsalicylic acid) for acute pain relief. In one aspect, the unit dose compositions reduce the occurrence and/or severity of heartburn in a human that takes OTC naproxen sodium for the treatment of acute pain. In another aspect, the unit dose compositions reduce the severity of heartburn in a human that takes OTC naproxen sodium for the treatment of acute pain.

Heartburn can be measured on different heartburn rating scales. The absence or presence of heartburn over a specified time can be measured on a nominal scale ("I have no heartburn" or "I have heartburn"). On rating instruments that measure the intensity of heartburn, the absence of heartburn can be measured as "no heartburn" on a categorical heartburn intensity scale; as 0 (zero) on a 0-to-10 numerical heartburn rating scale; or as 0 (zero) on a 0-to-100 mm linear, or visual analog, heartburn intensity rating scale. Consequently, the percentage of subjects who report "no heartburn" over the treatment period of a clinical study can be determined (e.g., 35% of the subjects using the unit oral dose composition had no heartburn, compared to 85% of the subjects using naproxen sodium, indicating a significant 50% difference, or reduction, in the occurrence of heartburn). Similarly, the percentage of subjects who report the occurrence of any heartburn over the treatment period of a clinical study can also be determined. Thus, for example, if 65% of the subjects using naproxen sodium had heartburn, compared to 15% of the subjects using the unit oral dose composition, these results identify 50% absolute difference in the occurrence of heartburn. In other words, there is about 77% relative risk reduction for a human using the unit oral dose composition compared to a human using the same dosage strength of naproxen sodium. In another aspect, when the clinical study includes subjects taking a placebo resulting in 16% with heartburn (i.e., comparable to 15% of the subjects using the unit oral dose composition), these results indicate that the unit oral dose composition prevents naproxen sodium-induced heartburn.

In another aspect, described herein are unit oral dose compositions for reducing the risk of occurrence and/or severity of heartburn in a human when taking naproxen sodium. In this aspect, the unit oral dose compositions prevent heartburn altogether when compared to the oral administration to the human of the same dosage strength of said naproxen sodium. In one aspect, the unit oral dose compositions reduce the risk of occurrence and/or severity of heartburn in a human when taking naproxen sodium by at least 10%, at least 20%, at least 30%, at least 40%, at least 50%, at least 60%, at least 70%, at least 80%, at least 90%, at least 95%, or up to 100% when compared to the oral administration to the human of the same dosage strength of said naproxen sodium in the absence of said famotidine.

Heartburn intensity scales also provide measurements of the severity (or intensity) of heartburn: by categories of heartburn intensity on a categorical heartburn intensity scale ("mild heartburn," "moderate heartburn," "severe heartburn"); by the numbers 1 through 10 on a numerical heartburn rating scale, where, for example, "1-3" represents mild heartburn, "4-6" represents moderate heartburn, and "7-10" represents "severe heartburn;" or on a linear, or visual analog, scale with ratings from 1 mm to 100 mm, which represents "severe heartburn." A subject's total experience with heartburn can be expressed as the sum of heartburn intensity ratings over a specified time, showing how much heartburn subjects experience as a result of using different compositions. In one aspect, summed heartburn severity can be measured over a specified period of time (e.g., over 1 hour, over 2 hours, over 4 hours, over 6 hours, over 8 hours, over 10 hours, over 12 hours, over 24 hours, over 48 hours) after only the initial dose and comparisons can be made between treatments. In another aspect, summed heartburn severity can be measured over a specified period of time (e.g., over 2 hours, over 4 hours, over 6 hours, over 8 hours, over 10 hours, over 12 hours, over 24 hours, over 48 hours) after multiple doses and comparisons can be made between treatments (e.g., subjects using only naproxen sodium report more severe heartburn than subjects using the unit oral dose composition).

In another aspect, the unit oral dose compositions reduce the severity of heartburn in a human by at least 10%, at least 20%, at least 30%, at least 40%, at least 50%, at least 60%, at least 70%, at least 80%, at least 90%, at least 95%, or up to 100% when compared to the oral administration to the human of the same dosage strength of said naproxen sodium over a specified period of time (e.g., over 1 hour, over 2 hours, over 4 hours, over 6 hours, over 8 hours, over 10 hours, over 12 hours, over 24 hours, over 48 hours).

In one aspect humans administered the unit oral dose compositions described herein report lower levels of heartburn severity over a specified period of time (e.g., over 1 hour, over 2 hours, over 4 hours, over 6 hours, over 8 hours, over 10 hours, over 12 hours, over 24 hours) after administration of a single unit oral dose composition than humans administered famotidine to treat naproxen sodium-induced heartburn that occurs after the administration of a single oral unit of naproxen sodium. In another aspect, summed heartburn severity over a specified period of time (e.g., over 1 hour, over 2 hours, over 4 hours, over 6 hours, over 8 hours, over 10 hours, over 12 hours, over 24 hours) is reduced by at least 10%, at least 20%, at least 30%, at least 40%, at least 50%, at least 60%, at least 70%, at least 80%, at least 90%, at least 95%, or up to 100% for humans administered a single unit oral dose composition described herein when compared to the single oral administration to the human of the same dosage strength of said naproxen sodium over the same specified period of time followed by the administration of famotidine to treat naproxen sodium-induced heartburn. In another aspect, summed heartburn severity for humans administered one, two, or three doses of the unit oral dose compositions described herein over a specified period of time (e.g., over 1 hour, over 2 hours, over 4 hours, over 6 hours, over 8 hours, over 10 hours, over 12 hours, over 24 hours) is reduced by at least 10%, at least 20%, at least 30%, at least 40%, at least 50%, at least 60%, at least 70%, at least 80%, at least 90%, at least 95%, or up to 100% when compared to the oral administration to the human of the same dosage strength of said naproxen sodium at the same treatment regimen followed by the administration of famotidine to treat naproxen-induced heartburn over the same specified period of time. These outcomes indicate that the co-administration of famotidine with naproxen sodium in the unit oral dose compositions) reduces the severity of heartburn more than treating naproxen-induced heartburn by administering famotidine after heartburn occurs.

The unit dose compositions described herein provide a reduction in the severity of heartburn pain and/or the prevention of heartburn pain in a human when compared to the oral administration to the same human of the same dosage strength of famotidine for the treatment of heartburn. Not wishing to be bound by theory, by blocking the receptor on gastric parietal cells that produce gastric acid and cause heartburn in the stomach and esophagus, famotidine also reduces the amount of gastric fluid produced by gastric parietal cells that can be refluxed into the esophagus. With less volume of gastric fluid, the stomach also empties faster, which can promote increased earlier absorption of naproxen sodium from the intestine. As a result, with reduced severity or non-occurrence of heartburn caused by the anti-secretory activity of famotidine, the human would experience enhanced analgesic activity (i.e., reduction of pain) from naproxen sodium due to increased early absorption of naproxen sodium. Upon administration of the unit oral dose composition the human would also experience a greater reduction in the severity of heartburn pain or prevention of heartburn pain.

Not wishing to be bound by theory, the concomitant sensation of heartburn lowers the threshold at which a human experiences acute pain. A human with heartburn is more sensitive to pain (i.e., has a lower pain threshold) and typically reports greater acute pain than when the human has no or minimal heartburn. As a result, the human with acute pain is less responsive to the anti-nociceptive activity of an administered analgesic such as naproxen sodium. Because the human with heartburn is more sensitive to acute pain and reports greater pain severity, the same human experiences less reduction in pain severity and less pain relief from the same dosage strength of an analgesic than when there is less or no heartburn. In contrast, when the human's pain threshold is not affected by heartburn (e.g., when treated with famotidine present in the unit oral dose naproxen sodium-famotidine compositions described herein), the subject experiences greater reduction in pain severity and more pain relief. Therefore, for subjects with acute pain who report heartburn induced by OTC NSAIDs like naproxen sodium, ibuprofen, and aspirin, the unit oral dose compositions described herein can result in greater analgesic activity when compared to only the use of naproxen sodium. As a result of reducing the severity and/or occurrence of heartburn induced by taking naproxen sodium, the unit oral dose compositions described herein provide enhanced pain reduction for the subject with naproxen sodium-induced heartburn when compared to when the subject with naproxen sodium-induced heartburn uses only orally administered naproxen sodium. As discussed above, the pain threshold is lowered for subjects with heartburn induced by taking naproxen sodium but restored by the administration of fast-dissolving famotidine, thus enhancing pain relief by the co-administered naproxen sodium in the unit oral dose composition. Also as discussed above, famotidine reduces the amount of gastric fluid produced by parietal cells, which means the stomach contains less gastric fluid. Here the stomach empties faster, which promotes earlier absorption of naproxen sodium from the intestine. By reducing the production of gastric fluid, famotidine further enhances greater and faster pain relief due to naproxen sodium. Moreover, as a result of an enhanced absorption of naproxen sodium, less naproxen sodium (i.e., smaller doses and/or fewer doses of naproxen sodium over 24 hours) may be required to produce equal pain relief ("equi-analgesia") compared to standard dosages of naproxen sodium (e.g., 220 mg, 440 mg) or to total daily dosages of naproxen sodium (e.g., 220 mg, 440 mg, 660 mg). The unit oral dose compositions described herein thus provide enhanced pain reduction for the subject with naproxen sodium-induced heartburn when compared to when the subject uses only orally administered naproxen sodium.

The unit oral dose compositions described herein effect the severity of acute pain. The sensation of pain can be measured utilizing different pain intensity rating scales. The absence or presence of pain, for example, can be measured on a nominal scale ("I have no pain" or "I have pain"). On rating instruments that measure the intensity of pain, the absence of pain is measured as "no pain" on a categorical pain intensity scale; as 0 on a 0-to-10 numerical rating scale; and as 0 on a 100-mm linear, or visual analog, scale. As measured on these pain intensity scales one can determine the percentage of subjects in a treatment group who report "no pain" over a specified period of time to identify differences in analgesic efficacy between treatments, showing, for example, that more subjects using the unit oral dose composition reported no pain than subjects using naproxen sodium over a specified period of time and how quickly subjects achieve this endpoint. Similarly, one can determine the percentage of subjects in a treatment group who require an additional analgesic over a specified period of time to identify differences in analgesic efficacy between treatments, showing, for example, that more subjects using naproxen sodium required an additional analgesic than subjects using the unit oral dose composition over a specified period of time.

Changes in pain over time can also be measured on pain intensity scales, which include: categories (mild, moderate, severe on a categorical scale; the numbers 1 through 10 in a numerical rating scale, where, for example, "1-3" represents mild pain, "4-6" represents moderate pain, and "7-10" represents "severe pain;" or ratings from 1 mm to 100 mm on a visual analog scale. Changes measured on these pain intensity scales can be expressed as pain intensity difference (PID) or as percentage difference in pain intensity (% PID) at a specified time. Or the effects on pain intensity can be expressed as the percentage of subjects with at least 50% reduction of pain (or "pain half-gone") over a specified period of time to identify differences in analgesic efficacy between treatments, showing, for example, that more subjects using the unit oral dose composition reported at least 50% pain reduction than subjects using naproxen sodium over a specified period of time and how quickly subjects achieve this endpoint.

In another aspect, the unit oral dose compositions reduce the severity of pain in a human by at least 10%, at least 20%, at least 30%, at least 40%, at least 50%, at least 60%, at least 70%, at least 80%, at least 90%, at least 95%, or up to 100% when compared to the oral administration to the human of the same dosage strength of said naproxen sodium over a specified period of time (e.g., over 1 hour, over 2 hours, over 4 hours, over 6 hours, over 8 hours, over 10 hours, over 12 hours, over 24 hours, over 48 hours).

In another aspect, differences in pain intensity are added as summed pain intensity differences (SPID) or as summed percentage pain intensity differences (% SPID) over a specified period of time (e.g., SPID4, indicating SPID over 4 hours, or % SPID4, indicating % SPID over 4 hours; or SPID24, indicating SPID over 24 hours, or % SPID24, indicating % SPID over 24 hours; or SPID48, indicating SPID over 48 hours, or % SPID48, indicating % SPID over 48 hours; etc.), representing the total pain reduction which a subject experiences. SPID and % SPID can thus be compared between treatments to identify differences in overall analgesia attributable to specific compositions, for example, showing that subjects using the unit oral dose composition reported more pain reduction than subjects using naproxen sodium.

The effect of the unit oral dose compositions described herein in relieving acute pain can also be measured directly on pain relief scales. These measure increasing degrees of relief: for example, on a categorical relief scale as the categories of "mild relief," "moderate relief," or "complete relief;" on a 0-to-10 numerical relief scale, where the number 10 represents "complete relief" and 1 to 9 represent an increasing extent of relief; or, on a visual analog scale, where a 100-mm rating represents "complete relief," with 1 to 99 mm ratings representing an increasing extent of relief. In one aspect, the percentage of subjects in a treatment group who report "moderate relief" on a categorical scale can be determined, with comparisons on this metric indicating analgesic differences attributable to each composition (e.g., more subjects using the unit oral dose composition reported moderate relief by 90 minutes than subjects using naproxen sodium). In another aspect, one can determine the percentage of subjects who report "complete relief" over a specified period of time to identify differences in analgesic efficacy between treatments, showing, for example, that more subjects using the unit oral dose composition reported complete relief than subjects using naproxen sodium over a specified period of time and how quickly subjects achieve the endpoint of complete relief.

In another aspect total pain relief ratings are summed to produce total pain relief (TOTPAR) scores over a specified period of time (e.g., TOTPAR4, indicating the total pain relief which a subject experienced over 4 hours). TOTPAR scores are compared between treatment groups to identify differences in analgesic efficacy, showing, for example, that subjects using the unit oral dose composition reported more relief of pain than subjects using naproxen sodium over a specified period of time.

In another aspect, the onset of analgesic activity after only the initial dose of the unit oral dose composition can be compared with only the initial dose of naproxen sodium on measurements, for example, of pain intensity; pain relief, total pain relief, summed pain intensity difference, summed percentage pain intensity difference during the first hour after administration (e.g., the initial 15 minutes, the initial 30 minutes, the initial 45 minutes, the initial 60 minutes) or over a specified period of time (e.g., the first 2 hours, over the first 4 hours, over the first 6 hours, over the first 8 hours); on measurements of the time to peak pain relief, the time to peak pain intensity difference, the time to peak % pain intensity difference; or on measurements of the percentage of subjects with at least moderate relief or with greater than moderate relief over the first hour (over the first 2 hours, over the first 4 hours, or over the first 6 hours, over the first 8 hours), indicating an earlier onset of action of the unit oral dose composition than naproxen sodium.

In another aspect the duration of pain reduction (i.e., PID or % PID, SPID or % SPID) can be examined at specified time points (e.g., 6 hours, 8 hours, 10 hours, 12 hours, 16 hours, 20 hours, 24 hours) after only the initial dose, indicating a longer duration of action of the unit oral dose composition than the initial dose of only naproxen sodium. In another aspect the duration of pain relief can be examined at later specified time points (e.g., 30 hours, 36 hours, 48 hours, at 72 hours), indicating, for example, that significantly more subjects using the unit oral dose composition still reported at least moderate relief of pain or that subjects using the unit oral dose composition reported greater pain reduction over 48 hours or 72 hours, for example, than subjects using the same number of doses of naproxen sodium at the same treatment regimen.

The unit oral dose compositions described herein provide enhanced pain reduction (measured by pain intensity) and/or greater pain relief (measured directly) when compared to orally administered naproxen sodium which is followed by famotidine administered orally to relieve the heartburn induced by naproxen sodium. Naproxen sodium taken in the unit oral dose composition containing famotidine provides greater pain reduction and/or greater pain relief to the human than naproxen sodium followed by administering famotidine to treat naproxen sodium-induced heartburn.

In one aspect humans administered the unit oral dose compositions described herein report lower levels of pain intensity from pre-treatment pain intensity, resulting in greater pain reduction over a specified period of time (e.g., over 1 hour, over 2 hours, over 4 hours, over 6 hours, over 8 hours, over 10 hours, over 12 hours, over 24 hours, over 48 hours) after administration of a single unit oral dose composition than humans administered famotidine to treat naproxen sodium-induced heartburn after it occurs. In one aspect humans administered the unit oral dose compositions described herein report lower levels of pain intensity from pre-treatment pain intensity at specific time points after administration of the unit dose composition (e.g., at about 15 minutes, at about 20 minutes, at about 30 minutes, at about 45 minutes, at about 60 minutes, at about 2 hours, at about 4 hours, at about 6 hours, at about 8 hours, at about 10 hours, at about 12 hours, at about 24 hours), resulting in greater percentage pain reduction (% pain intensity difference, or % PID) than humans administering famotidine to treat naproxen sodium-induced heartburn after it occurs.

In another aspect, humans administered the unit oral dose compositions described herein report lower levels of pain intensity from pre-treatment pain intensity, resulting in greater overall pain reduction (i.e., summed pain intensity difference, or SPID) over a specified period of time (e.g., SPID over 30 minutes, over 1 hour, over 2 hours, over 4 hours, over 6 hours, over 8 hours, over 10 hours, over 12 hour, over 24 hours) after the initial dose than humans administering famotidine to treat naproxen sodium-induced heartburn after it occurs.

In another aspect, humans administered the unit oral dose compositions described herein report lower levels of pain intensity from pre-treatment pain intensity after the initial dose, resulting in greater overall percentage pain reduction (% summed pain intensity difference, or % SPID) over a specified period of time than humans administering famotidine to treat naproxen sodium-induced heartburn after it occurs (e.g., over 1 hour (% SPID1), over 2 hours (% SPID2), over 4 hours (% SPID4), over 6 hours (% SPID6), over 8 hours (% SPID8), over 12 hours (% SPID12), over 24 hours (% SPID24).

In one aspect, SPID1 for the unit dose composition described herein is greater than SPID1 for naproxen sodium. In another aspect, SPID2 for the unit dose composition described herein is greater than SPID2 for naproxen sodium, SPID4 for the unit dose composition described herein is greater than SPID4 for naproxen sodium, SPID6 for the unit dose composition described herein is greater than SPID6 for naproxen sodium, SPID8 for the unit dose composition described herein is greater than SPID8 for naproxen sodium, SPID10 for the unit dose composition described herein is greater than SPID10 for naproxen sodium, SPID12 for the unit dose composition described herein is greater than SPID12 for naproxen sodium.

In another aspect, a single unit oral dose composition described herein provides % SPID4 that is greater than or the same as the % SPID4 for two doses of naproxen sodium. In another aspect, a single unit oral dose composition described herein provides % SPID8 that is greater than or the same as the % SPID8 for two doses of naproxen sodium. In another aspect, a single unit oral dose composition described herein provides % SPID10 that is greater than or the same as the % SPID10 for two doses of naproxen sodium. In another aspect, a single unit oral dose composition described herein provides % SPID12 that is greater than or the same as the % SPID12 for two doses of naproxen sodium.

In another aspect, humans administered a single unit oral dose composition described herein report greater levels of pain relief at specified time points (e.g., at about 15 minutes, at about 20 minutes, at about 30 minutes, at about 45 minutes, at about 60 minutes, at about 2 hours, at about 4 hours, at about 6 hours, at about 8 hours, at about 10 hours, at about 12 hours, at about 24 hours) after the initial dose when compared to humans administered famotidine to treat heartburn following one unit oral dose of naproxen sodium. In another aspect, humans administered a single unit oral dose composition described herein after the initial dose report greater levels of total pain relief (TOTPAR) over a specified period of time (e.g., over 2 hours (TOTPAR2), over 4 hours (TOTPAR4), over 6 hours (TOTPAR6), over 8 hours (TOTPAR8), over 12 hours (TOTPAR12), over 24 hours (TOTPAR24), etc.) than humans administering famotidine to treat heartburn following one unit oral dose of naproxen sodium.

In another aspect a greater percentage of humans administered the unit oral dose compositions described herein report at least moderate relief of pain over a specified period of time after the initial dose (e.g., over 30 minutes, over 1 hour, over 2 hours, over 4 hours, over 6 hours, over 8 hours, over 10 hours, over 12 hours, over 24 hours, over 48 hours) than humans administering famotidine to treat naproxen sodium-induced heartburn after it occurs. In another aspect a greater percentage of humans administered the unit oral dose compositions described herein report greater than moderate relief of pain over a specified period of time (e.g., over 30 minutes, over 1 hour, over 2 hours, over 4 hours, over 6 hours, over 8 hours, over 10 hours, over 12 hours, over 24 hours, over 48 hours) after the initial dose than humans administering famotidine to treat naproxen sodium-induced heartburn after it occurs.

In another aspect, pain reduction is increased by at least about 20% over the initial hour following the administration of the unit oral dose composition compared to a human who is only administered naproxen sodium at the same treatment regimen (i.e., the same dosage strength of naproxen sodium administered at the same dosing times). In another aspect, pain reduction is increased by at least about 20%, about 25%, about 30%, about 35%, about 40%, about 45%, about 50%, about 55%, about 60%, about 65%, about 70%, about 75%, about 80%, about 85%, about 90, about 95%, or about 100% over the initial hour following the administration of the unit oral dose composition compared to a human only administered naproxen sodium. In one aspect, the human is administered one solid dosage form of the unit oral dose composition over 1 hour. In another aspect, the human is administered two solid dosage forms of the unit oral dose composition over 1 hour.

In another aspect, pain reduction is increased by at least about 20% over the initial 2 hours following the administration of the unit oral dose composition compared to a human who is administered only naproxen sodium at the same treatment regimen. In another aspect, pain reduction is increased by at least about 20%, about 25%, about 30%, about 35%, about 40%, about 45%, about 50%, about 55%, about 60%, about 65%, about 70%, about 75%, about 80%, about 85%, about 90, about 95%, or about 100% over the initial 2 hours following the administration of the unit oral dose composition compared to a human only administered naproxen sodium. In one aspect, the human is administered one solid dosage form of the unit oral dose composition over 2 hours. In another aspect, the human is administered two solid dosage forms of the unit oral dose composition over 2 hours (i.e., with, or within 1 hour following, the initial dose).

In another aspect, pain reduction is increased by at least about 20% over the initial 4 hours following the administration of the unit oral dose composition compared to a human who is administered only naproxen sodium at the same treatment regimen. In another aspect, pain reduction is increased by at least about 25%, about 30%, about 35%, about 40%, about 45%, about 50%, about 55%, about 60%, about 65%, about 70%, about 75%, about 80%, about 85%, about 90, about 95%, or about 100% over the initial 4 hours following the administration of the unit oral dose composition compared to a human only administered naproxen sodium. In one aspect, the human is administered one solid dosage form of the unit oral dose composition over 4 hours. In another aspect, the human is administered two solid dosage forms of the unit oral dose composition over 4 hours (i.e., with, or within 1 hour following, the initial dose).

In another aspect, pain reduction is increased by at least about 20% over the initial 6 hours following the administration of the unit oral dose composition compared to a human who is administered only naproxen sodium at the same treatment regimen. In another aspect, pain reduction is increased by at least about 25%, about 30%, about 35%, about 40%, about 45%, about 50%, about 55%, about 60%, about 65%, about 70%, about 75%, about 80%, about 85%, about 90, about 95%, or about 100% over the initial 6 hours following the administration of the unit oral dose composition compared to a human only administered naproxen sodium. In one aspect, the human is administered one solid dosage form of the unit oral dose composition over 6 hours. In another aspect, the human is administered two solid dosage forms of the unit oral dose composition over 6 hours (i.e., with, or within 1 hour following, the initial dose).

In another aspect, pain reduction is increased by at least about 20% over the initial 8 hours following the administration of the unit oral dose composition compared to a human who is administered only naproxen sodium at the same treatment regimen. In another aspect, pain reduction is increased by at least about 25%, about 30%, about 35%, about 40%, about 45%, about 50%, about 55%, about 60%, about 65%, about 70%, about 75%, about 80%, about 85%, about 90, about 95%, or about 100% over the initial 8 hours following the administration of the unit oral dose composition compared to a human only administered naproxen sodium. In one aspect, the human is administered one solid dosage form of the unit oral dose composition over 8 hours. In another aspect, the human is administered two solid dosage forms of the unit oral dose composition over 8 hours (i.e., with, or within 1 hour following, the initial dose).

In another aspect, pain reduction is increased by at least about 20% over the initial 12 hours following the administration of the unit oral dose composition compared to a human who is administered only naproxen sodium at the same treatment regimen. In another aspect, pain reduction is increased by at least about 25%, about 30%, about 35%, about 40%, about 45%, about 50%, about 55%, about 60%, about 65%, about 70%, about 75%, about 80%, about 85%, about 90, about 95%, or about 100% over the initial 12 hours following the administration of the unit oral dose composition compared to a human only administered naproxen sodium. In one aspect, the human is administered one solid dosage form of the unit oral dose composition over 12 hours. In another aspect, the human is administered two solid dosage forms of the unit oral dose composition at the same treatment regimen over 12 hours (i.e., with, within 1 hour following, or within about 8 to 12 hours following the initial dose).

In another aspect, pain reduction is increased by at least about 20% over the initial 24 hours following the administration of the unit oral dose composition compared to a human who is administered only naproxen sodium at the same treatment regimen. In another aspect, pain reduction is increased by at least about 25%, about 30%, about 35%, about 40%, about 45%, about 50%, about 55%, about 60%, about 65%, about 70%, about 75%, about 80%, about 85%, about 90, about 95%, or about 100% over the initial 24 hours following the administration of the unit oral dose composition compared to a human only administered naproxen sodium.

In one aspect, pain reduction is increased by at least about 20% over the initial 24 hours following the administration of two solid dosage forms (e.g., tablets or capsules) of the unit oral dose composition compared to a human who is administered two solid dosage forms of only naproxen sodium at the same treatment regimen (e.g., the second dose with the initial dose, within 1 hour following the initial dose or within 8 to 12 hours following the initial dose). In another aspect, pain reduction is increased by at least about 25%, about 30%, about 35%, about 40%, about 45%, about 50%, about 55%, about 60%, about 65%, about 70%, about 75%, about 80%, about 85%, about 90, about 95%, or about 100% over the initial 24 hours following the administration of the unit oral dose composition compared to a human only administered naproxen sodium at the same treatment regimen. In one aspect, the human is administered three solid dosage forms of the unit oral dose compositions over 24 hours compared to a human who is administered only naproxen sodium at the same treatment regimen.

In one aspect, the unit oral dose composition provides enhanced pain reduction in said human who develops naproxen sodium-induced-heartburn when compared to the administration to said human of the same dosage strength of only naproxen sodium (i.e., in the absence of said famotidine). In another aspect, pain reduction is increased by at least about 20% over the initial 24 hours following the administration of the unit oral dose composition compared to said human who develops naproxen sodium-induced heartburn when administered the same dosage strength of only naproxen sodium at the same treatment regimen. In another aspect, pain reduction is increased by at least about 30% over the initial 24 hours following the administration of the unit oral dose composition compared to said human who develops naproxen sodium-induced heartburn at the same treatment regimen when administered the same dosage strength of only naproxen sodium. In another aspect, pain reduction is increased by at least about 40% over the initial 24 hours following the administration of the unit oral dose composition compared to said human who develops naproxen sodium-induced heartburn over the same treatment regimen when administered the same dosage strength of only naproxen sodium. In another aspect, pain reduction is increased by at least about 50% over the initial 24 hours following the administration of the unit oral dose composition compared to said human who develops naproxen sodium-induced heartburn over the same treatment regimen when administered the same dosage strength of only naproxen sodium.

In another aspect, pain reduction is increased by at least about 20% over the initial 8 hours following the administration of the unit oral dose composition compared to said human who develops naproxen sodium-induced heartburn over the same treatment regimen when administered the same dosage strength of only naproxen sodium. In another aspect, pain reduction is increased by at least about 30% over the initial 8 hours following the administration of the unit oral dose composition compared to said human who develops naproxen sodium-induced heartburn over the same treatment regimen when administered the same dosage strength of only naproxen sodium. In another aspect, pain reduction is increased by at least about 40% over the initial 8 hours following the administration of the unit oral dose composition compared to said human who develops naproxen sodium-induced heartburn over the same treatment regimen when administered the same dosage strength of only naproxen sodium. In another aspect, pain reduction is increased by at least about 50% over the initial 8 hours following the administration of the unit oral dose composition compared to said human who develops naproxen sodium-induced heartburn over the same treatment regimen when administered the same dosage strength of only naproxen sodium.

In one aspect, the unit oral dose composition provides enhanced pain reduction in said human when compared to the oral administration to said human of twice the dosage strength of orally administered naproxen sodium in the absence of said famotidine at the initial dose. In one aspect, the initial unit oral dose composition administered to the human is only one tablet or capsule, and the initial unit oral dose of naproxen sodium alone is two tablets or capsules, with comparisons of analgesic outcomes, as described above, between the two different dosage strengths of naproxen sodium. In one aspect, for example, the initial unit oral composition contains 220 mg of naproxen sodium, and the initial unit oral dose of naproxen sodium alone is 440 mg of naproxen sodium (signifying 50% less naproxen sodium). In another aspect, for example, the initial unit oral dose composition administered to the human is one tablet or capsule containing 220 mg of naproxen sodium followed by another tablet or capsule about within 1 hour, and no additional dose within a 24-hour dosing period (i.e., 2 doses within a 24-hour dosing period, for a total daily dose of 440 mg of naproxen sodium), and the initial unit oral dose of naproxen sodium alone is one 220 mg tablet or capsule followed by another tablet or capsule within 1 hour and by another tablet or capsule at about 8 to 12 hours later (i.e., 3 doses within a 24-hour dosing period, for a total daily dose of 660 mg of naproxen sodium), with comparisons of analgesic outcomes between the two different dosage strengths. In this example reduced amounts of naproxen sodium (e.g., 33% less) may be required to achieve at least the same level of pain reduction when using the unit oral dose compositions described herein.

Depending upon the dosage strengths of naproxen sodium and famotidine in the unit oral dose composition, the number of unit oral dose compositions that can be administered to the human can vary over a 24-hour period. The unit oral dose compositions can be administered to the human as a single administration or multiple administrations as needed in a 24-hour period. Depending upon the dosage strength of naproxen sodium in the unit oral dose composition, the total daily dose of naproxen sodium can be reduced from the maximum total daily dose of naproxen sodium (660 mg). In one aspect, the unit oral dose composition containing 220 mg of naproxen sodium can be administered as needed with, or within 1 hour following, the initial dose of the unit dose composition for a total of 2 doses (i.e., 440 mg of naproxen sodium) in a 24-hour period. In another aspect, the unit oral dose composition can be administered with, or within 1 hour following, the initial dose, followed by another dose of the unit dose composition 8 to 12 hours later for a total of three units (i.e., 660 mg of naproxen sodium) in a 24-hour period. In another aspect, two unit oral dose compositions can be administered together followed by third unit oral dose composition within 8 to 12 hours for a total of three units (i.e., 660 mg of naproxen sodium) in a 24-hour period. In another aspect, the unit oral dose composition containing 165 mg of naproxen sodium (i.e., 25% less naproxen sodium than the customary 220 mg dose of naproxen sodium) can be administered with, or within 1 hour following, the initial dose, followed by another dose of the unit dose composition 8 to 12 hours later for a total of three units (i.e., 495 mg of naproxen sodium) in a 24-hour period. In another aspect, the unit dose composition containing 165 mg of naproxen sodium can be administered as needed with, or within 1 hour following, the initial dose of the unit dose composition, for a total of 2 doses (i.e., 330 mg of naproxen sodium) in a 24-hour period. In another aspect, the unit oral dose composition containing 110 mg of naproxen sodium can be administered with, or within 1 hour following, the initial dose, followed by another dose of the unit dose composition 8 to 12 hours later for a total of three units (i.e., 330 mg of naproxen sodium) in a 24-hour period.

In another aspect, the number of unit oral dose compositions that can be administered to the human can vary over a 2- or 3-day period, depending on the duration and severity of acute pain and the subject's need for pain relief. The unit oral dose compositions can be administered to the human as multiple administrations as needed in each 24-hour period. Depending upon the dosage strength of naproxen sodium in the unit oral dose composition, the total amount of naproxen sodium taken over 3 days for treatment of severe acute pain, for example, can be reduced from the maximum total amount of naproxen sodium that can be administered (i.e., a total of 1,980 mg). In one aspect, one unit oral dose composition containing 220 mg of naproxen sodium can be administered with, or within 1 hour following, the initial dose, followed by another dose of the unit dose composition 8 to 12 hours later, for a total of three units (i.e., 660 mg of naproxen sodium) in the first 24-hour period; followed by a total of two units (i.e., 440 mg of naproxen sodium) in the second 24-hour period; followed by one unit in the third 24-hour period, for a total of 1,320 mg of naproxen sodium over 3 days. In another aspect, the unit oral dose composition containing 165 mg of naproxen sodium can be administered with, or within 1 hour following, the initial dose, followed by another dose of the unit dose composition 8 to 12 hours later, for a total of three units (i.e., 495 mg of naproxen sodium) in the initial 24-hour period; followed by a total of two units (i.e., 330 mg of naproxen sodium) in the second 24-hour period; followed by one unit in the third 24-hour period, for a total of 990 mg of naproxen sodium over 3 days. In another aspect, the unit dose composition containing 165 mg of naproxen sodium can be administered with, or within 1 hour following, the initial dose of the unit dose composition, for a total of 2 units (i.e., 330 mg of naproxen sodium) in the initial 24-hour period; followed by one unit (i.e., 165 mg of naproxen sodium) in the second 24-hour period; followed by one unit in the third 24-hour period, for a total of 660 mg of naproxen sodium over 3 days. In another aspect, the unit oral dose composition containing 110 mg of naproxen sodium can be administered with, or within 1 hour following, the initial dose, followed by another dose of the unit dose composition 8 to 12 hours later for a total of three units (i.e., 330 mg of naproxen sodium) in the initial 24-hour period; followed by two units (i.e., 220 mg of naproxen sodium) in the second 24-hour period; followed by one unit in the third 24-hour period, for a total of 660 mg of naproxen sodium over 3 days. In each instance, as discussed above, the unit oral dose compositions provide enhanced pain reduction in said human who develops naproxen sodium-induced heartburn when compared to naproxen sodium; as a result, the total amount of naproxen sodium is reduced per day and over 3 days when said human uses the unit oral dose compositions.

The unit oral dose compositions may be packaged in a variety of ways. Generally, an article for distribution includes a container that contains the unit oral dose composition in an appropriate form. Suitable containers are well known to those skilled in the art and include materials such as bottles (plastic and glass), sachets, foil blister packs, and the like. The container may also include a tamper proof assemblage to prevent indiscreet access to the contents of the package. In addition, the container typically has deposited thereon a label that describes the contents of the container and any appropriate warnings or instructions.

The unit oral dose compositions may, if desired, be presented in a pack or dispenser device which may contain one or more unit dosage forms. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for non-prescription drugs, or the approved product insert. Pharmaceutical compositions comprising a disclosed compound formulated in a compatible pharmaceutical carrier may also be prepared, placed in an appropriate container, and labeled for treatment of an indicated condition.

Aspects

Aspect 1. A method for reducing the severity of heartburn and/or the risk of the occurrence of heartburn in a human in need of taking naproxen sodium for the treatment of acute pain wherein the human is not experiencing heartburn prior to the oral administration of the unit oral dose composition comprising orally administering to the human of a unit oral dose composition comprising (i) naproxen sodium at a dosage from about 100 mg to about 440 mg per unit oral dose composition and (ii) famotidine at a dosage from about 3 mg to about 20 mg per unit oral dose composition, wherein the dissolution rate of famotidine in the unit oral dose composition in said human at a specified time within 45 minutes of administration of said unit oral dose composition to said human is greater than the dissolution rate of naproxen sodium in the unit oral dose composition in said human at the same specified time.

Aspect 2. The method of Aspect 1, wherein the famotidine in the unit oral dose composition has a dissolution rate that is about 10% to about 30% greater than the dissolution rate of naproxen sodium at about 5 minutes, at about 10 minutes, at about 15 minutes, at about 20 minutes, at about 30 minutes, or at 45 minutes after administration of the unit oral dose composition to the human.

Aspect 3. The method of Aspect 1, wherein the famotidine in the unit oral dose composition has a dissolution rate at about 10 minutes after administration of said unit oral dose composition to said human that is about 5 minutes to less than 10 minutes earlier than the time required for naproxen sodium in said unit oral dose composition to achieve the same dissolution rate after administration of the unit oral dose composition to the human.

Aspect 4. The method of Aspect 1, wherein the famotidine in the unit oral dose composition has a dissolution rate at about 15 minutes after administration of said unit oral dose composition to said human that is about 5 minutes to about 10 minutes earlier than the time required for naproxen sodium in said unit oral dose composition to achieve the same dissolution rate after administration of the unit oral dose composition to the human.

Aspect 5. The method of Aspect 1, wherein the famotidine in the unit oral dose composition has a dissolution rate at about 20 minutes after administration of said unit oral dose composition to said human that is about 5 minutes to about 15 minutes earlier than the time required for naproxen sodium in said unit oral dose composition to achieve the same dissolution rate after administration of the unit oral dose composition to the human.

Aspect 6. The method of Aspect 1, wherein the famotidine in the unit oral dose composition has a dissolution rate at about 30 minutes after administration of said unit oral dose composition to said human that is about 5 minutes to about 25 minutes earlier than the time required for naproxen sodium in said unit oral dose composition to achieve the same dissolution rate after administration of the unit oral dose composition to the human.

Aspect 7. The method of Aspect 1, wherein the famotidine in the unit oral dose composition has a dissolution rate at about 45 minutes after administration of said unit oral dose composition to said human that is about 5 minutes to about 40 minutes earlier than the time required for naproxen sodium in said unit oral dose composition to achieve the same dissolution rate after administration of the unit oral dose composition to the human.

Aspect 8. The method of any one of Aspects 1-7, wherein the unit oral dose composition comprises a bi-layer tablet comprising a first layer of famotidine and the second layer comprising naproxen sodium, wherein the famotidine comprises microparticles, nanoparticles, or a combination thereof.

Aspect 9. The method of any one of Aspects 1-7, wherein the unit oral dose composition comprises a core comprising naproxen sodium surrounded by a layer of famotidine, wherein the famotidine comprises microparticles, nanoparticles, or a combination thereof.

Aspect 10. The method of Aspect 8 or 9, wherein the famotidine has an average particle diameter of from about 1 micrometer to about 1,000 micrometers.

Aspect 11. The method of Aspect 8 or 9, wherein the famotidine has an average particle diameter of from about 10 nanometers to about 1,000 nanometers.

Aspect 12. The method of any one of Aspects 1-11, wherein the unit oral dose composition does not include a release-delaying agent or an enteric coating.

Aspect 13. The method of any one of Aspects 1-12, wherein the unit dose composition provides reduction of heartburn severity and/or reduction of the risk of the occurrence of heartburn in said human when compared to the oral administration to said human of the same oral dosage strength of said naproxen sodium in the absence of said famotidine.

Aspect 14. The method of any one of Aspects 1-12, wherein the unit dose composition provides an enhanced reduction of heartburn severity in said human when compared to the oral administration of the same oral dosage strength of said famotidine following heartburn induced by the same oral dosage strength of naproxen sodium administered to said human.

Aspect 15. The method of any one of Aspects 1-14, wherein the acute pain comprises acute pain of inflammation, acute pain or stiffness of rheumatic or arthritic conditions, minor pain of arthritis, acute joint and body pains, dysmenorrhea (period pain) acute muscular aches and strains, acute pain of ligamentous sprains, acute backache, minor aches and pains due to the common cold, minor aches and pains due to fever, acute headache, acute pain of minor surgery, acute toothache, occasional sleeplessness when associated with minor aches and pains, or any combination thereof.

Aspect 16. The method of any one of Aspects 1-15, wherein said unit oral dose composition provides enhanced pain reduction in said human when compared to the oral administration to said human of the same dosage strength of said naproxen sodium in the absence of said famotidine.

Aspect 17. The method of any one of Aspects 1-16, wherein said unit oral dose composition further provides enhanced fever reduction in said human when compared to the administration to said human of the same dosage strength of said naproxen sodium in the absence of said famotidine.

Aspect 18. The method of any one of Aspects 1-17, wherein naproxen sodium is from about 220 mg to about 240 mg per unit oral dose composition.

Aspect 19. The method of any one of Aspects 1-17, wherein naproxen sodium is about 110 mg to about 165 mg per unit oral dose composition.

Aspect 20. The method of any one of Aspects 1-17, wherein naproxen sodium is about 220 mg per unit oral dose composition.

Aspect 21. The method of any one of Aspects 1-17, wherein famotidine is from about 3 mg to about 20 mg per unit oral dose composition.

Aspect 22. The method of any one of Aspects 1-17, wherein famotidine is about 10 mg per unit oral dose composition.

Aspect 23. The method of any one of Aspects 1-17, wherein famotidine is about 13.33 mg per unit oral dose composition.

Aspect 24. The method of any one of Aspects 1-17, wherein naproxen sodium is from about 200 mg to about 240 mg per unit oral dose composition and famotidine is from about 3 mg to about 20 mg per unit oral dose composition.

Aspect 25. The method of any one of Aspects 1-17, wherein naproxen sodium is about 220 mg per unit oral dose composition and famotidine is from about 3 mg to about 20 mg per unit oral dose composition.

Aspect 26. The method of any one of Aspects 1-17, wherein naproxen sodium is from about 200 mg to about 240 mg per unit oral dose composition and famotidine is about 13.33 mg per unit oral dose composition.

Aspect 27. The method of any one of Aspects 1-26, wherein the unit oral dose composition further comprises acetaminophen at a dosage of about 50 mg to about 500 mg.

Aspect 28. The method of any one of Aspects 1-27, wherein the unit oral dose composition further comprises diphenhydramine HCl or citrate at a dosage of about 5 mg to about 50 mg.

Aspect 29. A unit oral dose composition comprising (i) naproxen sodium at a dosage from about 100 mg to about 440 mg per unit oral dose composition and (ii) famotidine at a dosage from about 3 mg to about 20 mg per unit oral dose composition, wherein the dissolution rate of famotidine in the unit oral dose composition in said human at a specified time within 45 minutes of administration of said unit oral dose composition to said human is greater than the dissolution rate of naproxen sodium in the unit oral dose composition in said human at the same specified time.

Aspect 30. The unit oral dose composition of Aspect 29, wherein the famotidine in the unit oral dose composition has a dissolution rate that is about 10% to about 30% greater than the dissolution rate of naproxen sodium at about 5 minutes, at about 10 minutes, at about 15 minutes, at about 20 minutes, at about 30 minutes, or at 45 minutes after administration of the unit oral dose composition to the human.

Aspect 31. The unit oral dose composition of Aspect 29, wherein the famotidine in the unit oral dose composition has a dissolution rate at about 10 minutes after administration of said unit oral dose composition to said human that is about 5 minutes to less than 10 minutes earlier than the time required for naproxen sodium in said unit oral dose composition to achieve the same dissolution rate after administration of the unit oral dose composition to the human.

Aspect 32. The unit oral dose composition of Aspect 29, wherein the famotidine in the unit oral dose composition has a dissolution rate at about 15 minutes after administration of said unit oral dose composition to said human that is about 5 minutes to about 10 minutes earlier than the time required for naproxen sodium in said unit oral dose composition to achieve the same dissolution rate after administration of the unit oral dose composition to the human.

Aspect 33. The unit oral dose composition of Aspect 29, wherein the famotidine in the unit oral dose composition has a dissolution rate at about 20 minutes after administration of said unit oral dose composition to said human that is about 5 minutes to about 15 minutes earlier than the time required for naproxen sodium in said unit oral dose composition to achieve the same dissolution rate after administration of the unit oral dose composition to the human.

Aspect 34. The unit oral dose composition of Aspect 29, wherein the famotidine in the unit oral dose composition has a dissolution rate at about 30 minutes after administration of said unit oral dose composition to said human that is about 5 minutes to about 25 minutes earlier than the time required for naproxen sodium in said unit oral dose composition to achieve the same dissolution rate after administration of the unit oral dose composition to the human.

Aspect 35. The unit oral dose composition of Aspect 29, wherein the famotidine in the unit oral dose composition has a dissolution rate at about 45 minutes after administration of said unit oral dose composition to said human that is about 5 minutes to about 40 minutes earlier than the time required for naproxen sodium in said unit oral dose composition to achieve the same dissolution rate after administration of the unit oral dose composition to the human.

Aspect 36. The unit oral dose composition of any one of Aspects 29-35, wherein the unit oral dose composition comprises a bi-layer tablet comprising a first layer of famotidine and the second layer comprising naproxen sodium, wherein the famotidine comprises microparticles, nanoparticles, or a combination thereof.

Aspect 37. The unit oral dose composition of any one of Aspects 29-35, wherein the unit oral dose composition comprises a core comprising naproxen sodium surrounded by a layer of famotidine, wherein the famotidine comprises microparticles, nanoparticles, or a combination thereof.

Aspect 38. The unit oral dose composition of Aspect 36 or 37, wherein the famotidine has an average particle diameter of from about 1 micrometer to about 1,000 micrometers.

Aspect 39. The unit oral dose composition of Aspect 36 or 37, wherein the famotidine has an average particle diameter of from about 10 nanometers to about 1,000 nanometers.

Aspect 40. The unit oral dose composition of any one of Aspects 29-39, wherein the unit oral dose composition does not include a release-delaying agent or an enteric coating.

Aspect 41. The unit oral dose composition of any one of Aspects 29-40, wherein naproxen sodium is from about 220 mg to about 240 mg per unit oral dose composition.

Aspect 42. The unit oral dose composition of any one of Aspects 29-40, wherein naproxen sodium is about 110 mg to about 165 mg per unit oral dose composition.

Aspect 43. The unit oral dose composition of any one of Aspects 29-40, wherein naproxen sodium is about 220 mg per unit oral dose composition.

Aspect 44. The unit oral dose composition of any one of Aspects 29-40, wherein famotidine is from about 3 mg to about 20 mg per unit oral dose composition.

Aspect 45. The unit oral dose composition of any one of Aspects 29-40, wherein famotidine is about 10 mg per unit oral dose composition.

Aspect 46. The unit oral dose composition of any one of Aspects 29-40, wherein famotidine is about 13.33 mg per unit oral dose composition.

Aspect 47. The unit oral dose composition of any one of Aspects 29-40, wherein naproxen sodium is from about 200 mg to about 240 mg per unit oral dose composition and famotidine is from about 3 mg to about 20 mg per unit oral dose composition.

Aspect 48. The unit oral dose composition of any one of Aspects 29-40, wherein naproxen sodium is about 220 mg per unit oral dose composition and famotidine is from about 3 mg to about 20 mg per unit oral dose composition.

Aspect 49. The unit oral dose composition of any one of Aspects 29-40, wherein naproxen sodium is from about 200 mg to about 240 mg per unit oral dose composition and famotidine is about 13.33 mg per unit oral dose composition.

Aspect 50. The unit oral dose composition of any one of Aspects 29-49, wherein the unit oral dose composition further comprises acetaminophen at a dosage of about 50 mg to about 500 mg.

Aspect 51. The unit oral dose composition of any one of Aspects 29-50, wherein the unit oral dose composition further comprises diphenhydramine HCl or citrate at a dosage of about 5 mg to about 50 mg.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

The invention claimed is:

1. A unit oral dose composition comprising (i) naproxen sodium at a dosage from about 100 mg to about 440 mg per unit oral dose composition and (ii) famotidine at a dosage from about 3 mg to about 20 mg per unit oral dose composition,
wherein the unit oral dose composition comprises a core comprising naproxen sodium surrounded by a layer comprising famotidine, wherein the naproxen sodium and the famotidine each have an average particle size, wherein the average particle size of naproxen sodium is greater than the average particle size of famotidine, and
wherein the unit oral dose composition does not include a release-delaying agent or an enteric coating.

2. The unit oral dose composition of claim 1, wherein the layer of famotidine has a thickness of from about 10 μm to about 500 μm.

3. The unit oral dose composition of claim 1, wherein the unit oral dose composition does not include a barrier layer.

4. The unit oral dose composition of claim 1, wherein famotidine and naproxen sodium are in a form of microparticles, nanoparticles, or a combination thereof.

5. The unit oral dose composition of claim 1, wherein the unit dose composition is a tablet having a shape of a disk, sphere, rhomboid, or oval or the unit dose composition is a caplet.

6. The unit oral dose composition of claim 1, wherein naproxen sodium is present in an amount of from about 220 mg to about 240 mg per unit oral dose composition.

7. The unit oral dose composition of claim 1, wherein naproxen sodium is present in an amount of from about 110 mg to about 165 mg per unit oral dose composition.

8. The unit oral dose composition of claim 1, wherein naproxen sodium is present in an amount of about 220 mg per unit oral dose composition.

9. The unit oral dose composition of claim 1, wherein famotidine is present in an amount of about 10 mg per unit oral dose composition.

10. The unit oral dose composition of claim 1, wherein famotidine is present in an amount of about 13.33 mg per unit oral dose composition.

11. The unit oral dose composition of claim 1, wherein naproxen sodium is present in an amount of from about 200 mg to about 240 mg per unit oral dose composition and famotidine is about 13.33 mg per unit oral dose composition.

12. The unit oral dose composition of claim 1, wherein the unit oral dose composition further comprises acetaminophen at a dosage of from about 50 mg to about 500 mg.

13. The unit oral dose composition of claim 1, wherein the unit oral dose composition further comprises diphenhydramine HCl or citrate at a dosage of from about 5 mg to about 50 mg.

* * * * *